(12) United States Patent
Manabe

(10) Patent No.: US 8,598,176 B2
(45) Date of Patent: Dec. 3, 2013

(54) PYRIDAZINE COMPOUND AND USE THEREOF

(75) Inventor: Akio Manabe, Sanda (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 133 days.

(21) Appl. No.: 13/324,718

(22) Filed: Dec. 13, 2011

(65) Prior Publication Data

US 2012/0083605 A1 Apr. 5, 2012

Related U.S. Application Data

(62) Division of application No. 12/085,957, filed as application No. PCT/JP2006/324132 on Nov. 28, 2006, now Pat. No. 8,258,136.

(30) Foreign Application Priority Data

Dec. 7, 2005 (JP) ................... 2005-353177
Feb. 22, 2006 (JP) ................... 2006-044993

(51) Int. Cl.
C07D 401/04 (2006.01)
C07D 403/04 (2006.01)
A61K 31/501 (2006.01)
A61P 31/00 (2006.01)

(52) U.S. Cl.
USPC ............... 514/252.02; 514/252.03; 544/238

(58) Field of Classification Search
USPC .................. 514/252.02, 252.03; 544/238
See application file for complete search history.

(56) References Cited

U.S. PATENT DOCUMENTS

| 7,629,342 B2 | 12/2009 | Ewing et al. |
| 7,655,649 B2 | 2/2010 | Bilodeau et al. |
| 2011/0059978 A1 | 3/2011 | Li et al. |
| 2011/0098269 A1 | 4/2011 | Becknell et al. |

FOREIGN PATENT DOCUMENTS

| EP | 0 429344 | 5/1991 |
| EP | 1 767 529 A1 | 3/2007 |
| EP | 1 775 290 A1 | 4/2007 |
| JP | 2006-022084 A | 1/2006 |
| JP | 2006-045192 A | 2/2006 |
| WO | WO 99/10331 A1 | 3/1999 |
| WO | WO 02/22587 | 3/2002 |
| WO | WO 2004/014865 | 2/2004 |
| WO | WO 2005/063762 A1 | 7/2005 |
| WO | WO 2008/009406 A1 | 1/2008 |

OTHER PUBLICATIONS

El-Dean et al., "Synthesis and antimicrobial activity of pyrazolo[3',4':4,3]pyrido[6,5-c]pyridazine and thieno[2,3-c]pyridazine derivatives," Pharmazie, 1998, 53(12):839-843.
Fromm et al., "Spirodihydroazafluorenes—a new type of cis-fixed photochromic molecule with rigid region B showing extremely fast back reaction," Journal of Photochemistry and Photobiology A: Chemistry, 2000, 135:85-89.
Helm et al., "Synthesis of Highly Substituted Pyridazines through Alkynyl Boronic Ester Cycloaddition Reactions," Angew. Chem. Ind. Ed., 2005, 44:3889-3892.
Klyuev et al., "Chromatographic-mass spectrometric study of azines of alkyl benzyl ketones and products of their thermal transformation," Zhurnal Organicheskoi Khimii, 1979, 15(11):2274-2280, with English abstract.
Padhy et al., "Synthesis and anti-microbial activity of some pyrimidine derivatives," Indian Journal of Chemistry, Apr. 2003, 42B:910-915.
Pfleger, et al., Tomato-Tobacco Mosaic Virus Disease, 2008, downloaded Oct. 12, 2010, http://www/extension.umn.edu/distribution/horticulture/dg1168.html.
Ellis, et al., Bacterial Diseases of Plants, 2008, http://ohioline.osu.edu/hvg-fact/3000/pdf/PP401_06.pdf, downloaded Oct. 12, 2010.
Cornell Univ., Plant Disease Diagnostic Clinic, Nematodes, Mar. 2009, http://plantclinic/cornell.edu/FactSheets/nematodes/nematodes.htm, downloaded Oct. 12, 2010.
Swift, Dodder A Plant Parasite, Aug. 28, 1996, downloaded Oct. 12, 2010, http://www.coop0ext.colostate.edu/TRA/dodder.html.
Myclobutanil (http://chinayifan.com/pages/myclobutanil-e.htm, downloaded Sep. 20, 2008).
Gonella, et al., Bull. Insectol., 61(1); 221-222 (2008).

*Primary Examiner* — James O Wilson
*Assistant Examiner* — Cecilia M Jaisle
(74) *Attorney, Agent, or Firm* — Foley & Lardner LLP

(57) ABSTRACT

A pyridazine compound of the formula:

(1)

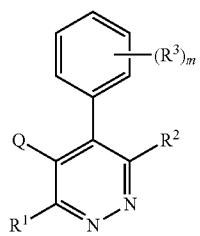

has an excellent plant disease controlling effect.

1 Claim, No Drawings

PYRIDAZINE COMPOUND AND USE THEREOF

CROSS-REFERENCE TO RELATED APPLICATION(S)

This application is a Divisional of U.S. patent application Ser. No. 12/085,957, filed Oct. 20, 2008, which is the National Phase of PCT/JP2006/324132, filed Nov. 28, 2006, and published as WO 2007/066601, on Jun. 14, 2007, which claims priority to Japanese Patent Application Nos. 2005-353177, filed Dec. 7, 2005, and 2006-044993, filed Feb. 22, 2006. The contents of these applications are incorporated herein by reference in their entirety.

TECHNICAL FIELD

The present invention relates to a pyridazine compound, its use and its production intermediate.

BACKGROUND ART

Conventionally, agricultural fungicides have been developed, and a lot of compounds having a fungicidal activity have been found. However, these compounds do not necessarily have a sufficient plant disease controlling effect in some cases, and novel compounds having a plant disease controlling effect are being searched.

DISCLOSURE OF THE INVENTION

The present inventors have intensively studied to find a compound having an excellent controlling activity on plant diseases, and resultantly found that a pyridazine compound of the following formula (1) has an excellent plant disease controlling activity, leading to completion of the present invention.

That is, the present invention is as described in the following [1] to [11].

[1] A pyridazine compound of the formula (1):

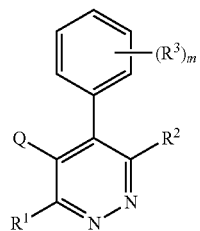

(1)

(wherein, $R^1$ represents a chlorine atom, bromine atom, C1-C4 alkyl group or C1-C4 alkoxy group, $R^2$ represents a C1-C4 alkyl group, $R^3$ represents a halogen atom, nitro group, cyano group, C1-C4 alkyl group optionally substituted with at least one halogen atom, C1-C4 alkoxy group optionally substituted with at least one halogen atom or C1-C4 alkylthio group optionally substituted with at least one halogen atom, m represents an integer of 0 to 5, and when m is an integer of 2 or more, $R^3$s are mutually the same or different, Q represents a 6-membered aromatic heterocyclic group having at least one nitrogen atom as a ring constituent atom, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom.).

(hereinafter, described as compound of the present invention.).

[2] The pyridazine compound according to [1], wherein in the formula (1), Q is an aromatic heterocyclic group selected from the group consisting of a pyridyl group, pyridazinyl group, pyrimidinyl group and pyrazinyl group, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom.

[3] The pyridazine compound according to [1], wherein in the formula (1), Q is an aromatic heterocyclic group selected from the group consisting of a 2-pyridyl group, 3-pyridazinyl group, 2-pyrimidinyl group, 4-pyrimidinyl group and 2-pyrazinyl group, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom.

[4] The pyridazine compound according to [1], wherein in the formula (1), Q is an aromatic heterocyclic group selected from the group consisting of a 2-pyridyl group, 2-pyrimidinyl group and 4-pyrimidinyl group, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom.

[5] The pyridazine compound according to [1], wherein in the formula (1), Q is a 2-pyridyl group, and the pyridyl group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom.

[6] The pyridazine compound according to any one of [1] to [5], wherein in the formula (1), m is 1 or 2.

[7] The pyridazine compound according to any one of [1] to [6], wherein in the formula (1), $R^1$ is a chlorine atom, bromine atom or methyl group and $R^2$ is a methyl group.

[8] A plant disease controlling agent comprising the pyridazine compound as described in any one of [1] to [7] as an active ingredient.

[9] A plant disease controlling method comprising a step of applying an effective amount of the pyridazine compound as described in any one of [1] to [7] to plants or soils growing a plant.

[10] Use of the pyridazine compound as described in any one of [1] to [7] for controlling plant diseases.

[11] A compound of the formula (2):

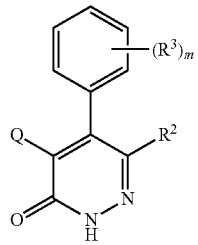

(2)

(wherein,

R² represents a C1-C4 alkyl group,

R³ represents a halogen atom, nitro group, cyano group, C1-C4 alkyl group optionally substituted with at least one halogen atom, C1-C4 alkoxy group optionally substituted with at least one halogen atom or C1-C4 alkylthio group optionally substituted with at least one halogen atom, m represents an integer of 0 to 5, and when m is an integer of 2 or more, R³s are mutually the same or different, Q represents a 6-membered aromatic heterocyclic group having at least one nitrogen atom as a ring constituent atom, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom.).

Next, the substituents on the compounds of the present invention will be described.

In the present invention, as R¹, R², R³ and Q, the following groups are mentioned.

Examples of the C1-C4 alkoxy group represented by R¹ include a methoxy group and ethoxy group.

Examples of the C1-C4 alkyl group represented by R² include a methyl group and ethyl group.

Examples of the C1-C4 alkyl group optionally substituted with at least one halogen atom represented by R³ include a methyl group, ethyl group, isopropyl group, tert-butyl group, trifluoromethyl group, difluoromethyl group and fluoromethyl group.

Examples of the C1-C4 alkoxy group optionally substituted with at least one halogen atom represented by R³ include a methoxy group, ethoxy group, isopropoxy group, trifluoromethoxy group, difluoromethoxy group, fluoromethoxy group, chlorodifluoromethoxy group, bromodifluoromethoxy group, 1,1,2,2-tetrafluoroethoxy group and 2,2,2-trifluoroethoxy group.

Examples of the C1-C4 alkylthio group optionally substituted with at least one halogen atom represented by R³ include a methylthio group, ethylthio group, trifluoromethylthio group and 1,1,2,2-tetrafluoroethylthio group.

The halogen atom represented by R³ include a fluorine atom, chlorine atom, bromine atom and iodine atom.

Examples of the 6-membered aromatic heterocyclic group having at least one nitrogen atom as a ring constituent atom include a pyridyl group, pyridazinyl group, pyrimidinyl group and pyrazinyl group. As the compound of the present invention, an embodiment is exemplified in which an atom adjacent to a nitrogen atom as a ring constituent atom of a 6-membered aromatic heterocyclic group represented by Q and a carbon atom of a pyridazine ring in the formula (1) are connected. Examples of the 6-membered aromatic heterocyclic group having at least one nitrogen atom as a ring constituent atom represented by Q in this embodiment include a 2-pyridyl group, 3-pyridazinyl group, 2-pyrimidinyl group, 4-pyrimidinyl group and 2-pyrazinyl group.

The 6-membered aromatic heterocyclic group having at least one nitrogen atom as a ring constituent atom represented by Q is optionally substituted with at least one substituent selected from the group consisting of halogen atoms (fluorine atom, chlorine atom, bromine atom and iodine atom), nitro group, cyano group, C1-C4 alkyl groups optionally substituted with at least one halogen atom (for example, methyl group, ethyl group, trifluoromethyl group, difluoromethyl group and fluoromethyl group) and C1-C4 alkoxy groups optionally substituted with at least one halogen atom (for example, methoxy group, ethoxy group, trifluoromethoxy group, difluoromethoxy group and fluoromethoxy group). Such a 6-membered aromatic heterocyclic group having at least one nitrogen atom as a ring constituent atom, for example, the following groups are mentioned.

2-pyridyl groups optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, such as a 2-pyridyl group, 3-methyl-2-pyridyl group, 3-chloro-2-pyridyl group, 3-fluoro-2-pyridyl group, 3-trifluoromethyl-2-pyridyl group, 3-methoxy-2-pyridyl group, 3-nitro-2-pyridyl group, 3-cyano-2-pyridyl group, 5-methyl-2-pyridyl group, 5-chloro-2-pyridyl group, 5-fluoro-2-pyridyl group, 5-trifluoromethyl-2-pyridyl group, 5-methoxy-2-pyridyl group, 4-methyl-2-pyridyl group, 4-chloro-2-pyridyl group, 4-fluoro-2-pyridyl group, 4-trifluoromethyl-2-pyridyl group, 4-methoxy-2-pyridyl group, 6-methyl-2-pyridyl group, 6-chloro-2-pyridyl group, 6-fluoro-2-pyridyl group, 6-trifluoromethyl-2-pyridyl group, 6-methoxy-2-pyridyl group, 3,5-dimethyl-2-pyridyl group, 3,5-dichloro-2-pyridyl group, 3,5-difluoro-2-pyridyl group, 3,6-dimethyl-2-pyridyl group, 3,6-dichloro-2-pyridyl group, 3,6-difluoro-2-pyridyl group, 6-chloro-3-trifluoromethyl-2-pyridyl group, 6-chloro-5-trifluoromethyl-2-pyridyl group, 3-chloro-5-trifluoromethyl-2-pyridyl group, 3-chloro-5-methoxy-2-pyridyl group, 3-nitro-5-methoxy-2-pyridyl group, 3-cyano-5-methoxy-2-pyridyl group, 5-methoxy-3-methyl-2-pyridyl group, 3-chloro-5-nitro-2-pyridyl group, 3,5,6-trichloro-2-pyridyl group, 3,5,6-trifluoro-2-pyridyl group and the like;

3-pyridazinyl groups optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, such as a 3-pyridazinyl group, 4-methyl-3-pyridazinyl group, 4-trifluoromethyl-3-pyridazinyl group, 4-cyano-3-pyridazinyl group, 4-nitro-3-pyridazinyl group, 4-methoxy-3-pyridazinyl group, 4-chloro-3-pyridazinyl group and the like;

2-pyrimidinyl groups optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, such as a 2-pyrimidinyl group, 5-methyl-2-pyrimidinyl group, 5-methoxy-2-pyrimidinyl group, 5-chloro-2-pyrimidinyl group, 5-fluoro-2-pyrimidinyl group, 5-nitro-2-pyrimidinyl group, 5-cyano-2-pyrimidinyl group, 5-trifluoromethyl-2-pyrimidinyl group, 4,6-dimethyl-2-pyrimidinyl group, 4,6-dimethoxy-2-pyrimidinyl group, 4,6-bis(trifluoromethyl)-2-pyrimidinyl group, 4-methoxy-6-methyl-2-pyrimidinyl group, 4-methyl-2-pyrimidinyl group, 4-methoxy-2-pyrimidinyl group, 4-chloro-2-pyrimidinyl group, 4-fluoro-2-pyrimidinyl group and the like;

4-pyrimidinyl groups optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, such as a 4-pyrimidinyl group, 5-methyl-4-pyrimidinyl group, 5-methoxy-4-pyrimidinyl group, 5-nitro-4-pyrimidinyl group, 5-cyano-4-pyrimidinyl group, 5-trifluoromethyl-4-pyrimidinyl group, 5-chloro-4-pyrimidinyl group, 5-fluoro-4-pyrimidinyl group, 2,5-dimethyl-4-pyrimidinyl group, 2-methyl-4-pyrimidinyl group, 2-methoxy-4-pyrimidinyl group, 2-chloro-4-pyrimidinyl group, 5-chloro-6-methyl-4-pyrimidinyl group, 5-chloro-2-methyl-4-pyrimidinyl group, 5-fluoro-6-methyl-4-pyrimidinyl group, 5-fluoro-2-methyl-4-pyrimidinyl group, 2-chloro-6-methyl-4-pyrimidinyl group and the like;

2-pyrazinyl groups optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, such as a 2-pyrazinyl group, 3-methyl-2-pyrazinyl group, 3-methoxy-2-pyrazinyl group, 3-trifluoromethylmethyl-2-pyrazinyl group, 3-cyano-2-pyrazinyl group, 3-nitro-2-pyrazinyl group, 3-chloro-2-pyrazinyl group and the like.

Examples of the phenyl group substituted with $(R^3)_m$ include a phenyl group; 4-methylphenyl group, 3-methylphenyl group, 2-methylphenyl group, 4-ethylphenyl group, 4-isopropylphenyl group, 4-tert-butylphenyl group, 4-(trifluoromethyl)phenyl group, 3-(trifluoromethyl)phenyl group, 4-chlorophenyl group, 3-chlorophenyl group, 2-chlorophenyl group, 4-fluorophenyl group, 3-fluorophenyl group, 2-fluorophenyl group, 4-methoxyphenyl group, 3-methoxyphenyl group, 4-ethoxyphenyl group, 4-(trifluoromethoxy)phenyl group, 4-nitrophenyl group, 4-cyanophenyl group, 4-(methylthio)phenyl group and 4-(trifluoromethylthio)phenyl group in which m is 1; and 2,4-dimethylphenyl group, 2,5-dimethylphenyl group, 3,4-dimethylphenyl group, 2,4-dichlorophenyl group, 2,5-dichlorophenyl group, 3,4-dichlorophenyl group, 2,3-difluorophenyl group, 2,4-difluorophenyl group, 2,5-difluorophenyl group, 3,4-difluorophenyl group, 3,5-difluorophenyl group, 4-chloro-2-fluorophenyl group, 2,4-dimethoxyphenyl group and 3,4-dimethoxyphenyl group in which m is 2.

As embodiments of the compound of the present invention, for example, the following pyridazine compounds are mentioned among compounds of the present invention.

Pyridazine compounds wherein $R^1$ is a chlorine atom or bromine atom, in the formula (1);

Pyridazine compounds wherein $R^1$ is a C1-C4 alkyl group, in the formula (1);

Pyridazine compounds wherein $R^1$ is a C1-C4 alkoxy group, in the formula (1);

Pyridazine compounds wherein $R^1$ is a chlorine atom and $R^2$ is a methyl group, in the formula (1);

Pyridazine compounds wherein $R^1$ is a methoxy group and $R^2$ is a methyl group, in the formula (1);

Pyridazine compounds wherein $R^1$ is a methyl group and $R^2$ is a methyl group, in the formula (1);

Pyridazine compounds wherein $R^3$ is a C1-C4 alkyl group optionally substituted with at least one halogen atom, C1-C4 alkoxy group optionally substituted with at least one halogen atom, or halogen atom, in the formula (1);

Pyridazine compounds wherein $R^3$ is a C1-C4 alkyl group or halogen atom, in the formula (1);

Pyridazine compounds wherein $R^3$ is a methyl group, trifluoromethyl group, chlorine atom, fluorine atom or methoxy group, in the formula (1);

Pyridazine compounds wherein $R^3$ is a methyl group, chlorine atom or fluorine atom, in the formula (1);

Pyridazine compounds wherein m is 1 or 2, in the formula (1);

Pyridazine compounds wherein m is 1, in the formula (1);

Pyridazine compounds wherein m is 2, in the formula (1);

Pyridazine compounds wherein m is 1 and $R^3$ is a substituent at 4-position of a benzene ring, in the formula (1);

Pyridazine compounds wherein m is 1, $R^3$ is a halogen atom, C1-C4 alkyl group optionally substituted with a halogen atom, or C1-C4 alkoxy group optionally substituted with at least one halogen atom, and $R^3$ is a substituent at 4-position of a benzene ring, in the formula (1);

Pyridazine compounds wherein m is 1, $R^3$ is a halogen atom or C1-C4 alkyl group optionally substituted with at least one halogen atom, and $R^3$ is a substituent at 4-position of a benzene ring, in the formula (1);

Pyridazine compounds wherein m is 1, $R^3$ is a halogen atom or C1-C4 alkyl group, and $R^3$ is a substituent at 4-position of a benzene ring, in the formula (1);

Pyridazine compounds wherein m is 1, $R^3$ is a methyl group, trifluoromethyl group, chlorine atom, fluorine atom or methoxy group, and $R^3$ is a substituent at 4-position of a benzene ring, in the formula (1);

Pyridazine compounds wherein m is 1, $R^3$ is a methyl group, chlorine atom or fluorine atom, and $R^3$ is a substituent at 4-position of a benzene ring, in the formula (1);

Pyridazine compounds wherein Q is an aromatic heterocyclic group selected from the group consisting of a pyridyl group, pyridazinyl group, pyrimidinyl group and pyrazinyl group, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, in the formula (1);

Pyridazine compounds wherein Q is an aromatic heterocyclic group selected from the group consisting of a 2-pyridyl group, 3-pyridazinyl group, 2-pyrimidinyl group, 4-pyrimidinyl group and 2-pyrazinyl group, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, in the formula (1);

Pyridazine compounds wherein Q is an aromatic heterocyclic group selected from the group consisting of a 2-pyridyl group, 2-pyrimidinyl group and 4-pyrimidinyl group, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, in the formula (1);

Pyridazine compounds wherein Q is a 2-pyridyl group, and the 2-pyridyl group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, in the formula (1);

Pyridazine compounds wherein Q is a 2-pyridyl group, and the 3-position of the 2-pyridyl group is substituted with a halogen atom, nitro group, cyano group, C1-C4 alkyl group optionally substituted with at least one halogen atom or C1-C4 alkoxy group optionally substituted with at least one halogen atom, in the formula (1);

Pyridazine compounds wherein Q is a 2-pyridyl group, and the 3-position of the 2-pyridyl group is substituted with a halogen atom or C1-C4 alkyl group optionally substituted with at least one halogen atom, in the formula (1);

Pyridazine compounds wherein Q is a 2-pyridyl group, the 3-position of the 2-pyridyl group is substituted with a halogen atom, nitro group, cyano group, methyl group, trifluoromethyl group or methoxy group, and other positions of the 2-pyridyl group are optionally substituted with at least one substituent selected from the group consisting of halogen atoms, nitro group, cyano group, methyl group, trifluoromethyl group and methoxy group, in the formula (1);

Pyridazine compounds wherein Q is a 2-pyridyl group, the 3-position of the 2-pyridyl group is substituted with a halogen atom or methyl group, and other positions of the 2-pyridyl group are optionally substituted with at least one substituent selected from the group consisting of halogen atoms, nitro group, cyano group, methyl group, trifluoromethyl group and methoxy group, in the formula (1);

Pyridazine compounds wherein Q is a 2-pyrimidinyl group, and the 2-pyrimidinyl group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, in the formula (1);

Pyridazine compounds wherein Q is a 4-pyrimidinyl group, and the 4-pyrimidinyl group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom, in the formula (1);

Pyridazine compounds wherein Q is a 4-pyrimidinyl group, and the 5-position of the 4-pyrimidinyl group is substituted with a halogen atom, nitro group, cyano group, C1-C4 alkyl group optionally substituted with at least one halogen atom or C1-C4 alkoxy groups optionally substituted with at least one halogen atom, in the formula (1);

Pyridazine compounds wherein Q is a 4-pyrimidinyl group, and the 5-position of the 4-pyrimidinyl group is substituted with a halogen atom or C1-C4 alkyl group optionally substituted with at least one halogen atom, in the formula (1);

Pyridazine compounds wherein Q is a 4-pyrimidinyl group, the 5-position of the 4-pyrimidinyl group is substituted with a halogen atom, nitro group, cyano group, methyl group, trifluoromethyl group or methoxy group, and other positions of the 4-pyrimidinyl group are optionally substituted with at least one substituent selected from the group consisting of halogen atoms, nitro group, cyano group, methyl group, trifluoromethyl group and methoxy group, in the formula (1);

Pyridazine compounds wherein Q is a 4-pyrimidinyl group, the 5-position of the 4-pyrimidinyl group is substituted with a halogen atom or methyl group, and other positions of the 4-pyrimidinyl group are optionally substituted with at least one substituent selected from the group consisting of halogen atoms, nitro group, cyano group, methyl group, trifluoromethyl group and methoxy group, in the formula (1).

Next, the method of producing a compound of the present invention will be described.

The compound of the present invention can be produced by, for example, the following (Production Method 1), (Production Method 2), (Production Method 3) or (Production Method 4).

(Production Method 1)

Compounds of the formula (1-1) wherein $R^1$ is a chlorine atom or bromine atom, among compounds of the present invention, can be produced by reacting a compound of the formula (2) with a halogenating agent.

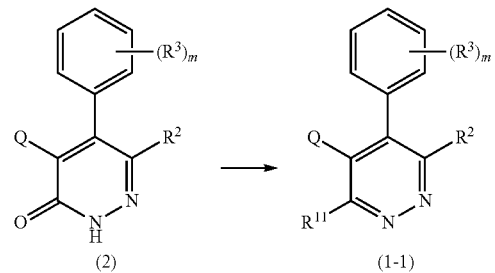

(wherein, $R^2$ represents a C1-C4 alkyl group, $R^3$ represents a halogen atom, nitro group, cyano group, C1-C4 alkyl group optionally substituted with at least one halogen atom, C1-C4 alkoxy group optionally substituted with at least one halogen atom or C1-C4 alkylthio group optionally substituted with at least one halogen atom, m represents an integer of 0 to 5, and when m is an integer of 2 or more, $R^3$s are mutually the same or different, Q represents a 6-membered aromatic heterocyclic group having at least one nitrogen atom as a ring constituent atom, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom.

$R^{11}$ represents a chlorine atom or bromine atom.).

The reaction is carried out in the absence or presence of a solvent.

Examples of the solvent to be used in the reaction include hydrocarbons such as toluene, xylene and the like, halogenated hydrocarbons such as chlorobenzene, dichlorobenzene and the like, and mixtures thereof.

Examples of the halogenating agent to be used in the reaction include chlorinating agents such as phosphorus oxychloride, phosphorus pentachloride and the like, and brominating agents such as phosphorus oxybromide, phosphorus pentabromide and the like. Mixtures of chlorinating agents or brominating agents are also used.

The amount of the halogenating agent to be used in the reaction is usually a proportion of 1 to 100 mol with respect to 1 mol of a compound of the formula (2).

The reaction temperature is usually in the range of 20 to 120° C., and the reaction time is usually in the range of 0.1 to 24 hours.

After completion of the reaction, for example, the reaction mixture is concentrated, to the resultant residue is added water or sodium bicarbonate water before extraction with an organic solvent, and the organic layer is subjected to post treatment operations such as drying, concentration and the like, thereby, a compound of the formula (1-1) can be isolated. The isolated compound of the formula (1-1) can also be further purified by chromatography, recrystallization and the like.

(Production Method 2)

Compounds of the formula (1-2) wherein $R^1$ is a C1-C4 alkoxy group, among compounds of the present invention, can be produced, for example, by reacting a compound of the formula (1-1) with an alcoholate compound of the formula:

(wherein, $R^{12}$ represents a C1-C4 alkoxy group)

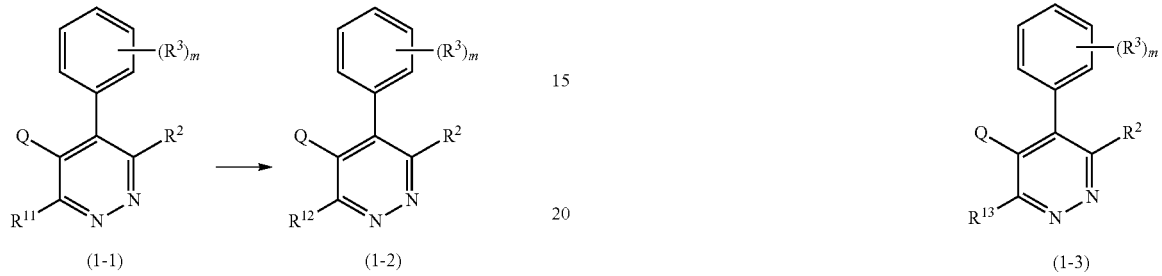

(wherein, $R^{11}$, $R^2$, $R^3$, m, Q and $R^{12}$ represent the same meanings as described above.).

The reaction is usually carried out in a solvent.

The solvent to be used in the reaction includes alcohols represented by $R^{12}H$, ethers such as tetrahydrofuran, 1,2-dimethoxyethane and the like, and mixtures thereof.

The amount of the alcoholate compound to be used in the reaction is usually a proportion of 1 to 20 mol with respect to 1 mol of a compound of the formula (1-1).

The reaction temperature is usually in the range of 0 to 120° C., and the reaction time is usually in the range of 1 to 72 hours.

After completion of the reaction, for example, water is added to the reaction mixture before extraction with an organic solvent, and the organic layer is subjected to post treatment operations such as drying, concentration and the like, thereby, a compound of the formula (1-2) can be isolated. The isolated compound of the formula (1-2) can also be further purified by chromatography, recrystallization and the like.

(Production Method 3)

Compounds of the formula (1-3) wherein $R^1$ is a C1-C4 alkyl group, among compounds of the present invention, can be produced by the following route.

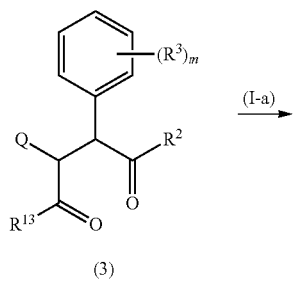

(wherein, $R^2$, $R^3$, m and Q represent the same meanings as described above, and $R^{13}$ represents a C1-C4 alkyl group.).

The process (I-a) will be described.

A compound of the formula (4) can be produced by reacting a compound of the formula (3) with hydrazine.

The reaction is usually carried out in a solvent.

Examples of the solvent to be used in the reaction include alcohols such as methanol, ethanol, propanol, isopropanol and the like, ethers such as tetrahydrofuran, 1,2-dimethoxyethane and the like, and mixtures thereof.

The amount of hydrazine to be used in the reaction is usually a proportion of 1 to 5 mol with respect to 1 mol of a compound of the formula (3). Hydrazine to be used in the reaction may also be its hydrate.

The reaction temperature is usually in the range of 0 to 80° C., and the reaction time is usually in the range of 1 to 24 hours.

After completion of the reaction, the reaction mixture is subjected to post treatment operations such as concentration and the like, thereby, a compound of the formula (4) can be isolated. The reaction mixture can also be used as it is in the process (I-b).

The process (I-b) will be described.

A compound of the present invention can be produced by reacting a compound of the formula (4) with an oxidizing agent.

The reaction is usually carried out in a solvent.

Examples of the oxidizing agent to be used in the reaction include platinum oxide ($PtO_2$) and lead dioxide ($PbO_2$).

Examples of the solvent to be used in the reaction include alcohols such as methanol, ethanol, propanol, isopropanol and the like, ethers such as tetrahydrofuran, 1,2-dimethoxyethane and the like, water, and mixtures thereof.

The amount of the oxidizing agent to be used in the reaction is usually a proportion of 1 to 5 mol with respect to 1 mol of a compound of the formula (4).

The reaction temperature of the reaction is usually in the range of 40 to 80° C., and the reaction time is usually in the range of 1 to 48 hours.

After completion of the reaction, for example, the reaction mixture is filtrated, and the resultant filtrate is subjected to post treatment operations such as concentration and the like, thereby, a compound of the present invention can be isolated.

The isolated compound of the present invention can also be further purified by operations such as chromatography, recrystallization and the like.

(Production Method 4)

Compounds of the formula (1-3) wherein $R^1$ is a C1-C4 alkyl group, among compounds of the present invention, can be produced by reacting a compound of the formula (5) with a base.

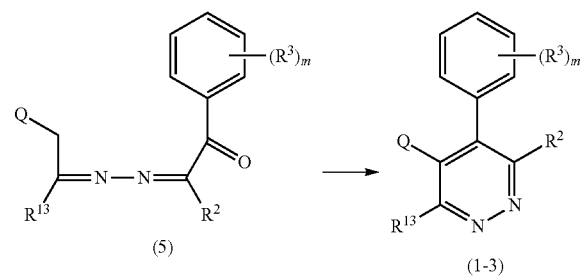

(wherein, $R^{13}$, $R^2$, $R^3$, m and Q represent the same meanings as described above.).

The reaction is usually carried out in a solvent.

Examples of the solvent to be used in the reaction include alcohols such as methanol, ethanol, propanol, isopropanol, tert-butanol and the like, ethers such as tetrahydrofuran, 1,2-dimethoxyethane and the like, and mixtures thereof.

Examples of the base to be used in the reaction include alkali metal hydroxides such as potassium hydroxide, sodium hydroxide and the like.

The amount of the base to be used in the reaction is usually a proportion of 1 to 2 mol with respect to 1 mol of a compound of the formula (5).

The reaction temperature is usually in the range of 0 to 100° C., and the reaction time is usually in the range of 0.1 to 8 hours.

After completion of the reaction, for example, the reaction mixture is mixed with water, extraction with an organic solvent is carried out, and the organic layer is subjected to post treatment operations such as drying, concentration and the like, thereby, a compound of the present invention can be isolated. The isolated compound of the present invention can also be further purified by chromatography, recrystallization and the like.

Next, the method of producing an intermediate of a compound of the present invention will be shown as a reference production method.

(Reference Production Method 1)

A compound of the formula (2) can be produced, for example, by reacting a compound of the formula (13) with hydrazine.

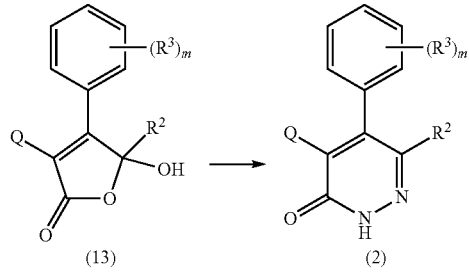

(wherein, $R^2$, $R^3$, m and Q represent the same meanings as described above.).

The reaction is usually carried out in a solvent.

Examples of the solvent to be used in the reaction include alcohols such as methanol, ethanol, propanol, isopropanol, butanol and the like, ethers such as tetrahydrofuran, 1,2-dimethoxyethane and the like, and mixtures thereof.

The amount of hydrazine to be used in the reaction is usually a proportion of 1 to 5 mol with respect to 1 mol of a compound of the formula (13). Hydrazine to be used in the reaction may also be its hydrate.

The reaction temperature is usually in the range of 0 to 120° C., and the reaction time is usually in the range of 0.2 to 24 hours.

After completion of the reaction, post treatment operations are carried out such as cooling of the reaction mixture to give deposited solid which is then filtrated, or concentration of the reaction mixture, and the like, thereby, a compound of the formula (2) can be isolated. The isolated compound of the formula (2) can also be further purified by chromatography, recrystallization and the like.

(Reference Production Method 2)

A compound of the formula (13) can be produced, for example, according to the following scheme.

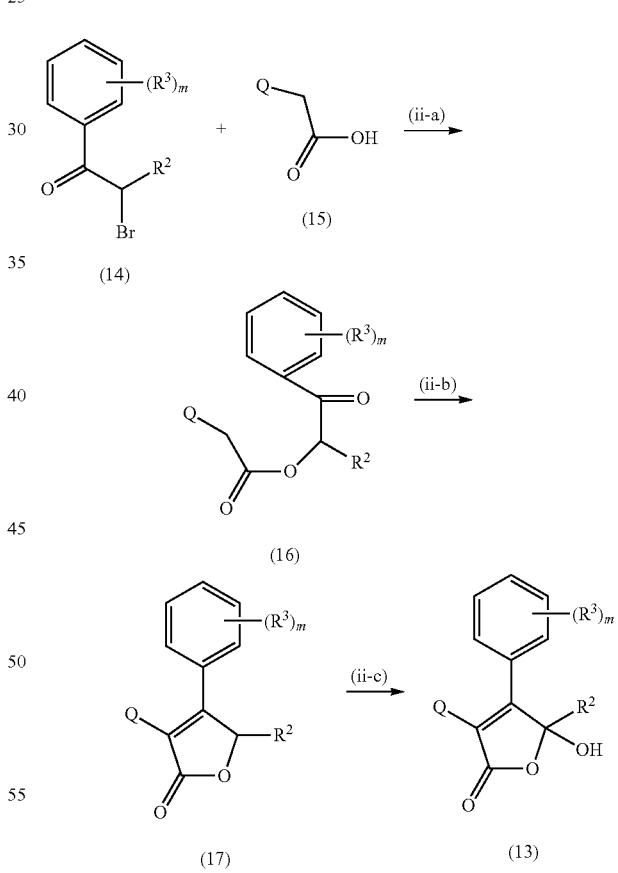

(wherein, $R^2$, $R^3$, m and Q represent the same meanings as described above.).

The production method as depicted in the above-described scheme is composed of a process (ii-a), a process (ii-b) and a process (ii-c).

The reaction of the process (ii-a) is carried out, for example, by mixing a compound of the formula (14); a compound of the formula (15) or its salt (for example, hydrochloride and the like); a non-cyclic tertiary amine compound such as triethylamine, diisopropylethylamine and the like; and a solvent.

Examples of the solvent to be used in the reaction include nitriles such as acetonitrile, propionitrile and the like, ethers such as tetrahydrofuran, 1,2-dimethoxyethane and the like, amides such as N,N-dimethylformamide (DMF) and the like, aromatic hydrocarbons such as toluene, xylene and the like, and mixtures thereof.

The amounts of the compound of the formula (15) and the non-cyclic tertiary amine to be used in the reaction are usually a proportion of 0.8 to 3 mol with respect to 1 mol of a compound of the formula (14).

The reaction temperature is usually in the range of 0 to 50° C., and the reaction time is usually in the range of 1 to 48 hours.

After completion of the reaction, for example, the reaction mixture is mixed with water, extraction with an organic solvent is carried out, and the organic layer is subjected to post treatment operations such as drying, concentration and the like, thereby, an ester compound of the formula (16) can be isolated. After completion of the reaction, the reaction mixture can also be used as it is in the process (ii-b).

The reaction of the process (ii-b) can be carried out, for example, by mixing a compound of the formula (16); at least one cyclic amine compound selected from the group consisting of 1,8-diazabicyclo[5.4.0]undec-7-ene (DBU), 1,5-diazabicyclo[4.3.0]non-5-ene (DBN) and 1,4-diazabicyclo[2.2.2]octane; and, if necessary, a solvent.

Examples of the solvent to be used in the reaction include nitriles such as acetonitrile, propionitrile and the like, ethers such as tetrahydrofuran, 1,2-dimethoxyethane and the like, amides such as N,N-dimethylformamide (DMF) and the like, aromatic hydrocarbons such as toluene, xylene and the like, and mixtures thereof.

The amount of the cyclic amine compound to be used in the invention is usually a proportion of 1 to 5 mol with respect to 1 mol of a compound of the formula (16).

The reaction temperature is usually in the range of 0 to 50° C., and the reaction time is usually in the range of 1 to 8 hours.

After completion of the reaction, for example, the reaction mixture is mixed with water, extraction with an organic solvent is carried out, and the organic layer is subjected to post treatment operations such as drying, concentration and the like, thereby, a compound of the formula (17) can be isolated. Further, after completion of the reaction, the reaction mixture can also be used as it is in the process (ii-c).

The reaction of the process (ii-c) can be carried out, for example, by allowing a compound of the formula (17) and oxygen to contact.

The reaction is usually carried out in a solvent.

Examples of the solvent to be used in the reaction include nitriles such as acetonitrile, propionitrile and the like, ethers such as tetrahydrofuran, 1,2-dimethoxyethane and the like, amides such as N,N-dimethylformamide (DMF) and the like, aromatic hydrocarbons such as toluene, xylene and the like, and mixtures thereof.

The oxygen to be used in the reaction may be oxygen itself, or a gas containing oxygen such as air and the like.

Contact of a compound of the formula (17) and oxygen is carried out, for example, by blowing oxygen into a solution of a compound of the formula (17), or stirring vigorously a solution of a compound of the formula (17) under an oxygen atmosphere.

The reaction temperature is usually in the range of 0 to 150° C., and the reaction time is usually in the range of 1 to 24 hours.

After completion of the reaction, the reaction mixture is mixed with dilute hydrochloric acid, extraction with an organic solvent is carried out, and the organic layer is subjected to post treatment operations such as drying, concentration and the like, thereby, a compound of the formula (13) can be isolated. The isolated compound of the formula (13) can also be further purified by chromatography, recrystallization and the like.

(Reference Production Method 3)

A compound of the formula (14) can be produced, for example, by reacting a compound of the formula (18) with bromine.

(wherein, $R^2$, $R^3$ and m represent the same meanings as described above.).

The reaction is usually carried out in a solvent.

Examples of the solvent to be used in the reaction include acetic acid.

The amount of bromine to be used in the invention is usually a proportion of 0.8 to 1.3 mol with respect to 1 mol of a compound of the formula (18).

The reaction temperature is usually in the range of −10 to 40° C., and the reaction time is usually in the range of 0.1 to 24 hours.

The reaction can also be carried out, for example, in the presence of a catalytic amount of hydrobromic acid.

After completion of the reaction, for example, the reaction mixture is concentrated or water is added to the reaction mixture and extraction with an organic solvent is performed, and the organic layer is washed with a sodium hydrogen carbonate aqueous solution and water, and subjected to post treatment operations such as drying, concentration and the like, thereby, a compound of the formula (14) can be isolated. The isolated compound of the formula (14) can also be further purified by chromatography, recrystallization and the like.

(Reference Production Method 4)

A compound of the formula (3) can be produced, for example, from a compound of the formula (22) and a compound of the formula (23), according to the following scheme.

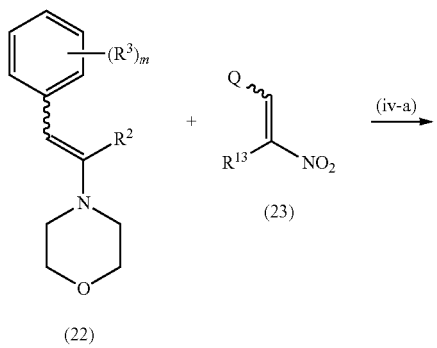

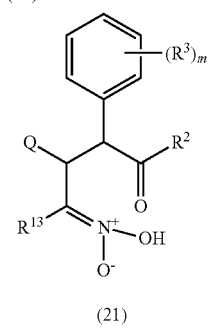

(wherein, $R^{13}$, $R^2$, $R^3$, m, $R^5$ and n represent the same meanings as described above.).

Process (iv-a)

A compound of the formula (21) can be produced by reacting a compound of the formula (23) and a compound of the formula (22).

The reaction is carried out in the presence or absence of a solvent.

The solvent to be used in the reaction includes hydrocarbons such as toluene, xylene and the like.

The amount of a compound of the formula (23) to be used in the invention is usually a proportion of 0.8 to 1.3 mol with respect to 1 mol of a compound of the formula (22).

The reaction temperature is usually in the range of 0 to 50° C., and the reaction time is usually in the range of 1 to 48 hours.

After completion of the reaction, usually, the reaction mixture is concentrated, and usually, the residue is used as it is in the reaction of the process (iv-b).

Process (iv-b)

A compound of the formula (3) can be produced by reacting a compound of the formula (21) with an acid.

The reaction is usually carried out in the presence of water and solvent.

Examples of the solvent to be used in the reaction include alcohols such as methanol, ethanol and the like, ethers such as tetrahydrofuran, 1,4-dioxane and the like, and mixtures thereof.

The reaction is usually carried out at a pH of around 2. Examples of the acid to be used include hydrochloric acid.

The reaction temperature is usually in the range of 0 to 30° C., and the reaction time is usually in the range of 1 to 48 hours.

After completion of the reaction, for example, a sodium hydrogen carbonate aqueous solution is added to the reaction mixture, extraction with an organic solvent is carried out, and the organic layer is concentrated, thereby, a compound of the formula (3) can be isolated. The isolated compound of the formula (3) can also be further purified by recrystallization, chromatography and the like.

A compound of the formula (22) can be produced, for example, according to a method described in J. Org. Chem., 32, pp. 213-214 (1967).

A compound of the formula (23) can be produced, for example, according to a method described in J. Med. Chem., 29, pp. 924-939 (1986).

(Reference Production Method 5)

A compound of the formula (5) can be produced by reacting a compound of the formula (24) and a compound of the formula (25) in the presence of an acid.

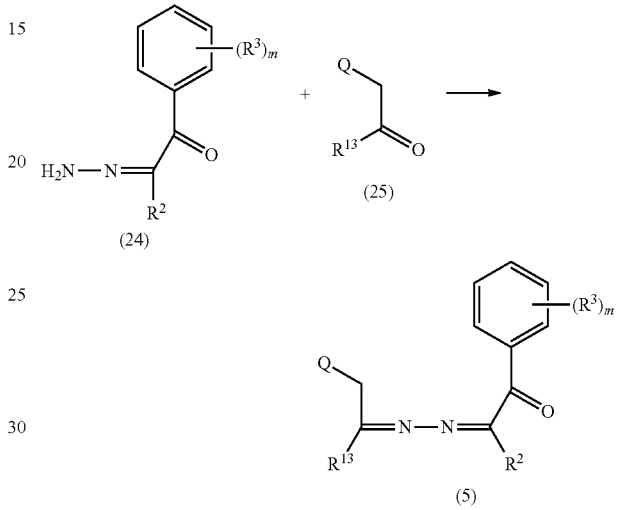

(wherein, $R^{13}$, $R^2$, $R^3$, m and Q represent the same meanings as described above.).

The reaction is usually carried out in the presence of a solvent.

Examples of the solvent to be used in the reaction include aromatic hydrocarbons such as toluene, xylene and the like.

Examples of the acid to be used in the reaction include organic sulfonic acids such as p-toluenesulfonic acid and the like.

The amount of a compound of the formula (25) to be used in the reaction is usually a proportion of 0.8 to 1.3 mol with respect to 1 mol of a compound of the formula (24). The amount of the acid to be used in the reaction is usually a proportion of 0.001 to 0.05 mol with respect to 1 mol of a compound of the formula (24).

The reaction temperature is usually in the range of 20 to 120° C., and the reaction time is usually in the range of 1 to 8 hours.

The reaction is carried out usually while dehydrating using a Dean-Stark trap.

After completion of the reaction, for example, (1) the reaction mixture is concentrated as it is, or (2) the reaction mixture is mixed with a sodium hydrogen carbonate aqueous solution, extraction with an organic solvent is carried out, and the organic layer is subjected to post treatment operations such as drying, concentration and the like, thereby, a compound of the formula (5) can be isolated. The isolated compound of the formula (5) can also be further purified by operations such as chromatography, recrystallization and the like.

(Reference Production Method 6)

A compound of the formula (24) can be produced by reacting a compound of the formula (26) with hydrazine.

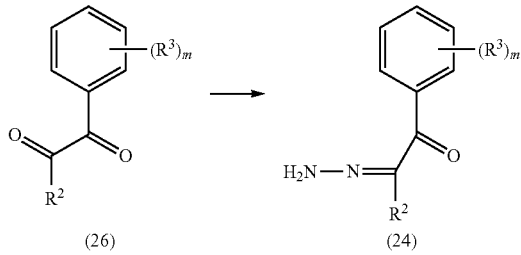

(wherein, $R^2$, $R^3$ and m represent the same meanings as described above.).

The reaction is carried out in the presence of a solvent.

Examples of the solvent to be used in the reaction include alcohols such as ethanol and the like.

The amount of hydrazine to be used in the reaction is usually a proportion of 0.8 to 1.3 mol with respect to 1 mol of a compound of the formula (26). Hydrazine to be used in the reaction may also be its hydrate.

The reaction temperature is usually in the range of 0 to 80° C., and the reaction time is usually in the range of 1 to 48 hours.

After completion of the reaction, the reaction mixture is subjected to post treatment operations such as concentration and the like, thereby, a compound of the formula (24) can be isolated. The isolated compound of the formula (24) can also be further purified by chromatography, recrystallization and the like.

As the compound of the formula (26), commercially available compounds can be used, or compounds produced according to, for example, a method described in J. Org. Chem., 43, pp. 2933-2935 (1978) or Synthesis, pp. 403-404, (1977) can be used. As the compound of the formula (25), compounds produced according to, for example, methods described in J. Med. Chem., 29, pp. 924-939 (1986); J. Med. Chem., 6, pp. 205-207 (1963); J. Org. Chem., 43, pp. 2286-2288 (1978) can be used.

(Reference Production Method 7)

A compound of the formula (2) can also be produced by, for example, reacting a compound of the formula (27) and a compound of the formula (24).

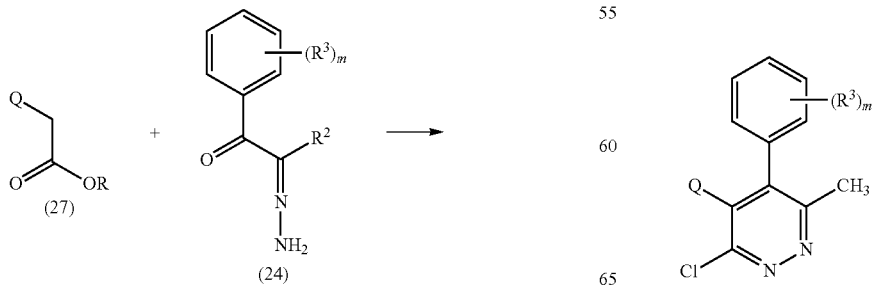

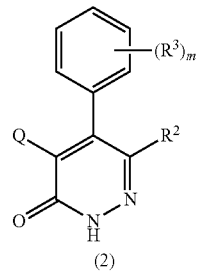

(wherein, $R^2$, $R^3$, m and Q represent the same meanings as described above, R represents a methyl group or ethyl group.).

The reaction is carried out usually in a solvent in the presence of a base.

Examples of the solvent to be used in the reaction include ethers such methanol, ethanol, tert-butanol, tetrahydrofuran, 1,2-dimethoxyethane, 1,4-dioxane and the like, aromatic hydrocarbons such as toluene, xylene and the like, amides such as N,N-dimethylformamide (DMF) and the like, nitriles such as acetonitrile, propionitrile and the like, and mixtures thereof.

Examples of the base to be used in the reaction include sodium methoxide, sodium ethoxide, potassium tert-butoxide, sodium hydride, 1,8-diazabicyclo[5.4.0]undec-7-ene (DBU), 1,5-diazabicyclo[4.3.0]non-5-ene (DBN), 1,4-diazabicyclo[2.2.2]octane and the like.

The amounts of the compound of the formula (24) and the base to be used in the reaction are usually a proportion of 0.8 to 2 mol with respect to 1 mol of a compound of the formula (27).

The reaction temperature is usually in the range of 20 to 120° C., and the reaction time is usually in the range of 1 to 24 hours.

After completion of the reaction, (1) water is added to the reaction mixture, and if necessary, an acid is added to this, then, the mixture is cooled to give deposited solid which is then filtrated, or (2) the reaction mixture is extracted with an organic solvent, and the organic layer is subjected to operations such as concentration and the like, thereby, a compound of the formula (2) can be isolated. The isolated compound of the formula (2) can also be further purified by chromatography, recrystallization and the like.

Next, specific examples of the compound of the present invention will be shown.

Pyridazine compound of the formula (1-a):

Pyridazine compound of the formula (1-b):

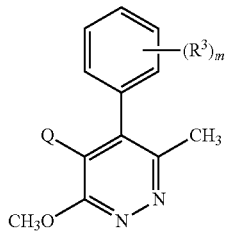
(1-b)

Pyridazine compound of the formula (1-c):

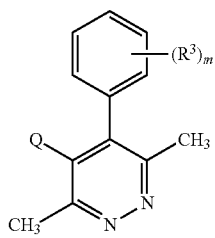
(1-c)

In the formula (1-a), formula (1-b) or formula (1-c), $(R^3)_m$ and Q represent one of combinations of substituents shown in (Table 1) to (Table 4).

(provided that, in the column of $(R^3)_m$ in the tables, a description of only "–" means that m is 0).

TABLE 1

| $(R^3)_m$ | Q |
|---|---|
| 4-Cl | 2-pyridyl |
| 4-Cl | 3-methyl-2-pyridyl |
| 4-Cl | 3-chloro-2-pyridyl |
| 4-Cl | 3-fluoro-2-pyridyl |
| 4-Cl | 3-trifluoromethyl-2-pyridyl |
| 4-Cl | 3-methoxy-2-pyridyl |
| 4-Cl | 5-methyl-2-pyridyl |
| 4-Cl | 5-chloro-2-pyridyl |
| 4-Cl | 5-fluoro-2-pyridyl |
| 4-Cl | 5-trifluoromethyl-2-pyridyl |
| 4-Cl | 5-methoxy-2-pyridyl |
| 4-Cl | 4-methyl-2-pyridyl |
| 4-Cl | 4-chloro-2-pyridyl |
| 4-Cl | 4-fluoro-2-pyridyl |
| 4-Cl | 4-trifluoromethyl-2-pyridyl |
| 4-Cl | 4-methoxy-2-pyridyl |
| 4-Cl | 6-methyl-2-pyridyl |
| 4-Cl | 6-chloro-2-pyridyl |
| 4-Cl | 6-fluoro-2-pyridyl |
| 4-Cl | 6-trifluoromethyl-2-pyridyl |
| 4-Cl | 6-methoxy-2-pyridyl |
| 4-Cl | 3,5-dimethyl-2-pyridyl |
| 4-Cl | 3,5-dichloro-2-pyridyl |
| 4-Cl | 3,5-difluoro-2-pyridyl |
| 4-Cl | 3,6-dimethyl-2-pyridyl |
| 4-Cl | 3,6-dichloro-2-pyridyl |
| 4-Cl | 3,6-difluoro-2-pyridyl |
| 4-Cl | 6-chloro-3-trifluoromethyl-2-pyridyl |
| 4-Cl | 6-chloro-5-trifluoromethyl-2-pyridyl |

TABLE 2

| $(R^3)_m$ | Q |
|---|---|
| 4-Cl | 3-chloro-5-trifluoromethyl-2-pyridyl |
| 4-Cl | 3,5,6-trichloro-2-pyridyl |
| 4-Cl | 3,5,6-trifluoro-2-pyridyl |
| 4-CH$_3$ | 3-methyl-2-pyridyl |
| 4-F | 3-methyl-2-pyridyl |
| 4-OCH$_3$ | 3-methyl-2-pyridyl |
| — | 3-methyl-2-pyridyl |
| 4-CF$_3$ | 3-methyl-2-pyridyl |
| 3-Cl | 3-methyl-2-pyridyl |
| 3,4-Cl$_2$ | 3-methyl-2-pyridyl |
| 2-F,4-Cl | 3-methyl-2-pyridyl |
| 4-Cl | 2-pyrimidinyl |
| 4-Cl | 5-methyl-2-pyrimidinyl |
| 4-Cl | 5-methoxy-2-pyrimidinyl |
| 4-Cl | 5-chloro-2-pyrimidinyl |
| 4-Cl | 5-fluoro-2-pyrimidinyl |
| 4-Cl | 4,6-dimethyl-2-pyrimidinyl |
| 4-Cl | 4,6-bis(trifluoromethyl)-2-pyrimidinyl |
| 4-Cl | 4-methyl-2-pyrimidinyl |
| 4-Cl | 4-methoxy-2-pyrimidinyl |
| 4-Cl | 4-chloro-2-pyrimidinyl |
| 4-Cl | 4-fluoro-2-pyrimidinyl |
| 4-Cl | 4-pyrimidinyl |
| 4-Cl | 5-methyl-4-pyrimidinyl |
| 4-Cl | 5-methoxy-4-pyrimidinyl |
| 4-Cl | 5-chloro-4-pyrimidinyl |
| 4-Cl | 5-fluoro-4-pyrimidinyl |
| 4-Cl | 2,5-dimethyl-4-pyrimidinyl |
| 4-Cl | 2-methyl-4-pyrimidinyl |

TABLE 3

| $(R^3)_m$ | Q |
|---|---|
| 4-Cl | 2-methoxy-4-pyrimidinyl |
| 4-Cl | 2-chloro-4-pyrimidinyl |
| 4-Cl | 5-chloro-6-methyl-4-pyrimidinyl |
| 4-Cl | 5-chloro-2-methyl-4-pyrimidinyl |
| 4-Cl | 5-fluoro-6-methyl-4-pyrimidinyl |
| 4-Cl | 5-fluoro-2-methyl-4-pyrimidinyl |
| 4-Cl | 2-chloro-6-methyl-4-pyrimidinyl |
| 4-Cl | 3-pyridazinyl |
| 4-Cl | 4-methyl-3-pyridazinyl |
| 4-Cl | 4-chloro-2-pyridazinyl |
| 4-Cl | 2-pyrazinyl |
| 4-Cl | 3-methyl-2-pyrazinyl |
| 4-Cl | 3-chloro-2-pyrazinyl |

TABLE 4

| $(R^3)_m$ | Q |
|---|---|
| 4-CH$_3$ | 3-chloro-2-pyridyl |
| 4-F | 3-chloro-2-pyridyl |
| 4-OCH$_3$ | 3-chloro-2-pyridyl |
| — | 3-chloro-2-pyridyl |
| 4-CF$_3$ | 3-chloro-2-pyridyl |
| 3-Cl | 3-chloro-2-pyridyl |
| 3,4-Cl$_2$ | 3-chloro-2-pyridyl |
| 2-F,4-Cl | 3-chloro-2-pyridyl |
| 4-Cl | 3-nitro-2-pyridyl |
| 4-Cl | 3-cyano-2-pyridyl |
| 4-Cl | 3-chloro-5-methoxy-2-pyridyl |
| 4-Cl | 3-nitro-5-methoxy-2-pyridyl |
| 4-Cl | 3-cyano-5-methoxy-2-pyridyl |
| 4-Cl | 5-methoxy-3-methyl-2-pyridyl |
| 4-Cl | 3-chloro-5-nitro-2-pyridyl |
| 4-Cl | 4-methoxy-6-methyl-2-pyrimidinyl |
| 4-Cl | 4,6-dimethoxy-2-pyrimidinyl |
| 4-Cl | 5-nitro-4-pyrimidinyl |
| 4-Cl | 5-cyano-4-pyrimidinyl |
| 4-Cl | 5-trifluoromethyl-4-pyrimidinyl |
| 4-Cl | 4-trifluoromethyl-3-pyridazinyl |

TABLE 4-continued

| (R³)ₘ | Q |
|---|---|
| 4-Cl | 4-cyano-3-pyridazinyl |
| 4-Cl | 4-nitro-2-pyridazinyl |
| 4-Cl | 4-methoxy-3-pyridazinyl |
| 4-Cl | 3-trifluoromethyl-2-pyrazinyl |
| 4-Cl | 3-cyano-2-pyrazinyl |
| 4-Cl | 3-nitro-2-pyrazinyl |
| 4-Cl | 3-methoxy-2-pyrazinyl |
| 4-CH₃ | 3-fluoro-2-pyridyl |
| 4-F | 3-fluoro-2-pyridyl |
| 4-OCH₃ | 3-fluoro-2-pyridyl |
| — | 3-fluoro-2-pyridyl |
| 4-CF₃ | 3-fluoro-2-pyridyl |
| 3-Cl | 3-fluoro-2-pyridyl |
| 3,4-Cl₂ | 3-fluoro-2-pyridyl |
| 2-F,4-Cl | 3-fluoro-2-pyridyl |
| 4-CH₃ | 3,5-difluoro-2-pyridyl |
| 4-F | 3,5-difluoro-2-pyridyl |
| 4-OCH₃ | 3,5-difluoro-2-pyridyl |
| — | 3,5-difluoro-2-pyridyl |
| 4-CF₃ | 3,5-difluoro-2-pyridyl |
| 3-Cl | 3,5-difluoro-2-pyridyl |
| 3,4-Cl₂ | 3,5-difluoro-2-pyridyl |
| 2-F,4-Cl | 3,5-difluoro-2-pyridyl |
| 4-CH₃ | 3,5-dichloro-2-pyridyl |
| 4-F | 3,5-dichloro-2-pyridyl |
| 4-OCH₃ | 3,5-dichloro-2-pyridyl |
| — | 3,5-dichloro-2-pyridyl |
| 4-CF₃ | 3,5-dichloro-2-pyridyl |
| 3-Cl | 3,5-dichloro-2-pyridyl |
| 3,4-Cl₂ | 3,5-dichloro-2-pyridyl |
| 2-F,4-Cl | 3,5-dichloro-2-pyridyl |
| 4-CH₃ | 5-chloro-3-fluoro-2-pyridyl |
| 4-F | 5-chloro-3-fluoro-2-pyridyl |
| 4-OCH₃ | 5-chloro-3-fluoro-2-pyridyl |
| — | 5-chloro-3-fluoro-2-pyridyl |
| 4-CF₃ | 5-chloro-3-fluoro-2-pyridyl |
| 3-Cl | 5-chloro-3-fluoro-2-pyridyl |
| 3,4-Cl₂ | 5-chloro-3-fluoro-2-pyridyl |
| 2-F,4-Cl | 5-chloro-3-fluoro-2-pyridyl |
| 4-CH₃ | 3-chloro-5-methoxy-2-pyridyl |
| 4-F | 3-chloro-5-methoxy-2-pyridyl |
| 4-OCH₃ | 3-chloro-5-methoxy-2-pyridyl |
| — | 3-chloro-5-methoxy-2-pyridyl |
| 4-CF₃ | 3-chloro-5-methoxy-2-pyridyl |
| 3-Cl | 3-chloro-5-methoxy-2-pyridyl |
| 3,4-Cl₂ | 3-chloro-5-methoxy-2-pyridyl |
| 2-F,4-Cl | 3-chloro-5-methoxy-2-pyridyl |

Specific examples of production intermediates of compounds of the present invention are shown below.

Compound of the following formula (2-a)

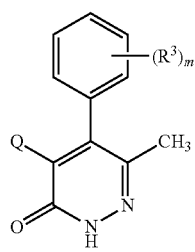

(2-a)

Compound of the following formula (13-a)

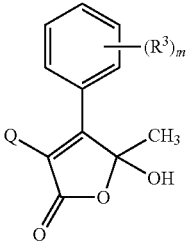

(13-a)

Compound of the following formula (16-a)

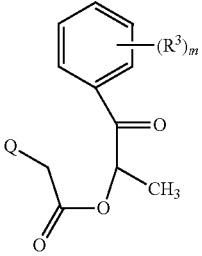

(16-a)

Compound of the following formula (17-a)

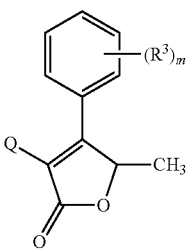

(17-a)

Compound of the following formula (3-a)

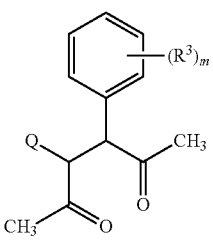

(3-a)

Compound of the following formula (4-a)

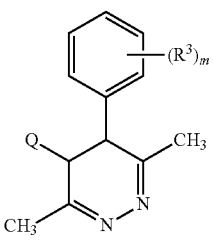

(4-a)

Compound of the following formula (5-a)

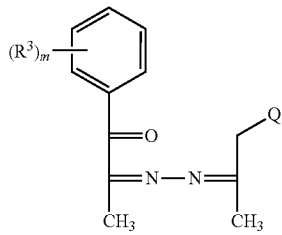

Compound of the following formula (21-a)

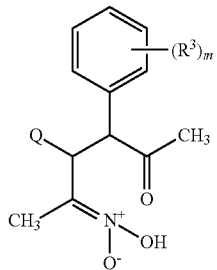

In the formula (2-a), formula (13-a), formula (16-a), formula (17-a), formula (3-a), formula (4-a), formula (5-a) and formula (21-a), $(R^3)_m$ and Q represent one of combinations of substituents shown in (Table 5) to (Table 8).

(provided that, in the column of $(R^3)_m$ in the tables, a description of only "–" means that m is 0).

TABLE 5

| $(R^3)_m$ | Q |
| --- | --- |
| 4-Cl | 2-pyridyl |
| 4-Cl | 3-methyl-2-pyridyl |
| 4-Cl | 3-chloro-2-pyridyl |
| 4-Cl | 3-fluoro-2-pyridyl |
| 4-Cl | 3-trifluoromethyl-2-pyridyl |
| 4-Cl | 3-methoxy-2-pyridyl |
| 4-Cl | 5-methyl-2-pyridyl |
| 4-Cl | 5-chloro-2-pyridyl |
| 4-Cl | 5-fluoro-2-pyridyl |
| 4-Cl | 5-trifluoromethyl-2-pyridyl |
| 4-Cl | 5-methoxy-2-pyridyl |
| 4-Cl | 4-methyl-2-pyridyl |
| 4-Cl | 4-chloro-2-pyridyl |
| 4-Cl | 4-fluoro-2-pyridyl |
| 4-Cl | 4-trifluoromethyl-2-pyridyl |
| 4-Cl | 4-methoxy-2-pyridyl |
| 4-Cl | 6-methyl-2-pyridyl |
| 4-Cl | 6-chloro-2-pyridyl |
| 4-Cl | 6-fluoro-2-pyridyl |
| 4-Cl | 6-trifluoromethyl-2-pyridyl |
| 4-Cl | 6-methoxy-2-pyridyl |
| 4-Cl | 3,5-dimethyl-2-pyridyl |
| 4-Cl | 3,5-dichloro-2-pyridyl |
| 4-Cl | 3,5-difluoro-2-pyridyl |
| 4-Cl | 3,6-dimethyl-2-pyridyl |
| 4-Cl | 3,6-dichloro-2-pyridyl |
| 4-Cl | 3,6-difluoro-2-pyridyl |
| 4-Cl | 6-chloro-3-trifluoromethyl-2-pyridyl |
| 4-Cl | 6-chloro-5-trifluoromethyl-2-pyridyl |

TABLE 6

| $(R^3)_m$ | Q |
| --- | --- |
| 4-Cl | 3-chloro-5-trifluoromethyl-2-pyridyl |
| 4-Cl | 3,5,6-trichloro-2-pyridyl |
| 4-Cl | 3,5,6-trifluoro-2-pyridyl |
| 4-CH₃ | 3-methyl-2-pyridyl |
| 4-F | 3-methyl-2-pyridyl |
| 4-OCH₃ | 3-methyl-2-pyridyl |
| — | 3-methyl-2-pyridyl |
| 4-CF₃ | 3-methyl-2-pyridyl |
| 3-Cl | 3-methyl-2-pyridyl |
| 3,4-Cl₂ | 3-methyl-2-pyridyl |
| 2-F,4-Cl | 3-methyl-2-pyridyl |
| 4-Cl | 2-pyrimidinyl |
| 4-Cl | 5-methyl-2-pyrimidinyl |
| 4-Cl | 5-methoxy-2-pyrimidinyl |
| 4-Cl | 5-chloro-2-pyrimidinyl |
| 4-Cl | 5-fluoro-2-pyrimidinyl |
| 4-Cl | 4,6-dimethyl-2-pyrimidinyl |
| 4-Cl | 4,6-bis(trifluoromethyl)-2-pyrimidinyl |
| 4-Cl | 4-methyl-2-pyrimidinyl |
| 4-Cl | 4-methoxy-2-pyrimidinyl |
| 4-Cl | 4-chloro-2-pyrimidinyl |
| 4-Cl | 4-fluoro-2-pyrimidinyl |
| 4-Cl | 4-pyrimidinyl |
| 4-Cl | 5-methyl-4-pyrimidinyl |
| 4-Cl | 5-methoxy-4-pyrimidinyl |
| 4-Cl | 5-chloro-4-pyrimidinyl |
| 4-Cl | 5-fluoro-4-pyrimidinyl |
| 4-Cl | 2,5-dimethyl-4-pyrimidinyl |
| 4-Cl | 2-methyl-4-pyrimidinyl |

TABLE 7

| $(R^3)_m$ | Q |
| --- | --- |
| 4-Cl | 2-methoxy-4-pyrimidinyl |
| 4-Cl | 2-chloro-4-pyrimidinyl |
| 4-Cl | 5-chloro-6-methyl-4-pyrimidinyl |
| 4-Cl | 5-chloro-2-methyl-4-pyrimidinyl |
| 4-Cl | 5-fluoro-6-methyl-4-pyrimidinyl |
| 4-Cl | 5-fluoro-2-methyl-4-pyrimidinyl |
| 4-Cl | 2-chloro-6-methyl-4-pyrimidinyl |
| 4-Cl | 3-pyridazinyl |
| 4-Cl | 4-methyl-3-pyridazinyl |
| 4-Cl | 4-chloro-2-pyridazinyl |
| 4-Cl | 2-pyrazinyl |
| 4-Cl | 3-methyl-2-pyrazinyl |
| 4-Cl | 3-chloro-2-pyrazinyl |

TABLE 8

| $(R^3)_m$ | Q |
| --- | --- |
| 4-CH₃ | 3-chloro-2-pyridyl |
| 4-F | 3-chloro-2-pyridyl |
| 4-OCH₃ | 3-chloro-2-pyridyl |
| — | 3-chloro-2-pyridyl |
| 4-CF₃ | 3-chloro-2-pyridyl |
| 3-Cl | 3-chloro-2-pyridyl |
| 3,4-Cl₂ | 3-chloro-2-pyridyl |
| 2-F,4-Cl | 3-chloro-2-pyridyl |
| 4-Cl | 3-nitro-2-pyridyl |
| 4-Cl | 3-cyano-2-pyridyl |
| 4-Cl | 3-chloro-5-methoxy-2-pyridyl |
| 4-Cl | 3-nitro-5-methoxy-2-pyridyl |
| 4-Cl | 3-cyano-5-methoxy-2-pyridyl |
| 4-Cl | 5-methoxy-3-methyl-2-pyridyl |
| 4-Cl | 3-chloro-5-nitro-2-pyridyl |
| 4-Cl | 4-methoxy-6-methyl-2-pyrimidinyl |
| 4-Cl | 4,6-dimethoxy-2-pyrimidinyl |

TABLE 8-continued

| (R³)ₘ | Q |
|---|---|
| 4-Cl | 5-nitro-4-pyrimidinyl |
| 4-Cl | 5-cyano-4-pyrimidinyl |
| 4-Cl | 5-trifluoromethyl-4-pyrimidinyl |
| 4-Cl | 4-trifluoromethyl-3-pyridazinyl |
| 4-Cl | 4-cyano-3-pyridazinyl |
| 4-Cl | 4-nitro-2-pyridazinyl |
| 4-Cl | 4-methoxy-3-pyridazinyl |
| 4-Cl | 3-trifluoromethyl-2-pyrazinyl |
| 4-Cl | 3-cyano-2-pyrazinyl |
| 4-Cl | 3-nitro-2-pyrazinyl |
| 4-Cl | 3-methoxy-2-pyrazinyl |
| 4-CH₃ | 3-fluoro-2-pyridyl |
| 4-F | 3-fluoro-2-pyridyl |
| 4-OCH₃ | 3-fluoro-2-pyridyl |
| — | 3-fluoro-2-pyridyl |
| 4-CF₃ | 3-fluoro-2-pyridyl |
| 3-Cl | 3-fluoro-2-pyridyl |
| 3,4-Cl₂ | 3-fluoro-2-pyridyl |
| 2-F,4-Cl | 3-fluoro-2-pyridyl |
| 4-CH₃ | 3,5-difluoro-2-pyridyl |
| 4-F | 3,5-difluoro-2-pyridyl |
| 4-OCH₃ | 3,5-difluoro-2-pyridyl |
| — | 3,5-difluoro-2-pyridyl |
| 4-CF₃ | 3,5-difluoro-2-pyridyl |
| 3-Cl | 3,5-difluoro-2-pyridyl |
| 3,4-Cl₂ | 3,5-difluoro-2-pyridyl |
| 2-F,4-Cl | 3,5-difluoro-2-pyridyl |
| 4-CH₃ | 3,5-dichloro-2-pyridyl |
| 4-F | 3,5-dichloro-2-pyridyl |
| 4-OCH₃ | 3,5-dichloro-2-pyridyl |
| — | 3,5-dichloro-2-pyridyl |
| 4-CF₃ | 3,5-dichloro-2-pyridyl |
| 3-Cl | 3,5-dichloro-2-pyridyl |
| 3,4-Cl₂ | 3,5-dichloro-2-pyridyl |
| 2-F,4-Cl | 3,5-dichloro-2-pyridyl |
| 4-CH₃ | 5-chloro-3-fluoro-2-pyridyl |
| 4-F | 5-chloro-3-fluoro-2-pyridyl |
| 4-OCH₃ | 5-chloro-3-fluoro-2-pyridyl |
| — | 5-chloro-3-fluoro-2-pyridyl |
| 4-CF₃ | 5-chloro-3-fluoro-2-pyridyl |
| 3-Cl | 5-chloro-3-fluoro-2-pyridyl |
| 3,4-Cl₂ | 5-chloro-3-fluoro-2-pyridyl |
| 2-F,4-Cl | 5-chloro-3-fluoro-2-pyridyl |
| 4-CH₃ | 3-chloro-5-methoxy-2-pyridyl |
| 4-F | 3-chloro-5-methoxy-2-pyridyl |
| 4-OCH₃ | 3-chloro-5-methoxy-2-pyridyl |
| — | 3-chloro-5-methoxy-2-pyridyl |
| 4-CF₃ | 3-chloro-5-methoxy-2-pyridyl |
| 3-Cl | 3-chloro-5-methoxy-2-pyridyl |
| 3,4-Cl₂ | 3-chloro-5-methoxy-2-pyridyl |
| 2-F,4-Cl | 3-chloro-5-methoxy-2-pyridyl |

Compound of the following formula (15-a);

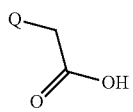
(15-a)

Compound of the following formula (27-a);

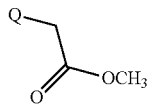
(27-a)

Compound of the following formula (27-b);

(27-b)

Compound of the following formula (23-a);

(23-a)

Compound of the following formula (25-a);

(25-a)

In the formula (15-a), formula (27-a), formula (27-b), formula (23-a) and formula (25-a), Q represents one of substituents shown in (Table 9) to (Table 11).

TABLE 9

| Q |
|---|
| 2-pyridyl |
| 3-methyl-2-pyridyl |
| 3-chloro-2-pyridyl |
| 3-fluoro-2-pyridyl |
| 3-trifluoromethyl-2-pyridyl |
| 3-methoxy-2-pyridyl |
| 5-methyl-2-pyridyl |
| 5-chloro-2-pyridyl |
| 5-fluoro-2-pyridyl |
| 5-trifluoromethyl-2-pyridyl |
| 5-methoxy-2-pyridyl |
| 4-methyl-2-pyridyl |
| 4-chloro-2-pyridyl |
| 4-fluoro-2-pyridyl |
| 4-trifluoromethyl-2-pyridyl |
| 4-methoxy-2-pyridyl |
| 6-methyl-2-pyridyl |
| 6-chloro-2-pyridyl |
| 6-fluoro-2-pyridyl |
| 6-trifluoromethyl-2-pyridyl |
| 6-methoxy-2-pyridyl |
| 3,5-dimethyl-2-pyridyl |
| 3,5-dichloro-2-pyridyl |
| 3,5-difluoro-2-pyridyl |
| 3,6-dimethyl-2-pyridyl |
| 3,6-dichloro-2-pyridyl |
| 3,6-difluoro-2-pyridyl |
| 6-chloro-3-trifluoromethyl-2-pyridyl |
| 6-chloro-5-trifluoromethyl-2-pyridyl |

TABLE 10

| Q |
|---|
| 3-chloro-5-trifluoromethyl-2-pyridyl |
| 3,5,6-trichloro-2-pyridyl |
| 3,5,6-trifluoro-2-pyridyl |
| 2-pyrimidinyl |
| 5-methyl-2-pyrimidinyl |
| 5-methoxy-2-pyrimidinyl |
| 5-fluoro-2-pyrimidinyl |
| 5-fluoro-2-pyrimidinyl |
| 4,6-dimethyl-2-pyrimidinyl |
| 4,6-bis(trifluoromethyl)-2-pyrimidinyl |
| 4-methyl-2-pyrimidinyl |
| 4-methoxy-2-pyrimidinyl |
| 4-chloro-2-pyrimidinyl |
| 4-fluoro-2-pyrimidinyl |
| 4-pyrimidinyl |
| 5-methyl-4-pyrimidinyl |
| 5-methoxy-4-pyrimidinyl |
| 5-chloro-4-pyrimidinyl |
| 5-fluoro-4-pyrimidinyl |
| 2,5-dimethyl-4-pyrimidinyl |
| 2-methyl-4-pyrimidinyl |
| 2-methoxy-4-pyrimidinyl |
| 2-chloro-4-pyrimidinyl |
| 5-chloro-6-methyl-4-pyrimidinyl |
| 5-chloro-2-methyl-4-pyrimidinyl |
| 5-fluoro-6-methyl-4-pyrimidinyl |
| 5-fluoro-2-methyl-4-pyrimidinyl |
| 2-chloro-6-methyl-4-pyrimidinyl |
| 3-pyridazinyl |

TABLE 11

| Q |
|---|
| 4-methyl-3-pyridazinyl |
| 4-chloro-2-pyridazinyl |
| 2-pyrazinyl |
| 3-methyl-2-pyrazinyl |
| 3-chloro-2-pyrazinyl |
| 3-nitro-2-pyridyl |
| 3-cyano-2-pyridyl |
| 3-chloro-5-methoxy-2-pyridyl |
| 3-nitro-5-methoxy-2-pyridyl |
| 3-cyano-5-methoxy-2-pyridyl |
| 5-methoxy-3-methyl-2-pyridyl |
| 3-chloro-5-nitro-2-pyridyl |
| 4-methoxy-6-methyl-2-pyrimidinyl |
| 4,6-dimethoxy-2-pyrimidinyl |
| 5-nitro-4-pyrimidinyl |
| 5-cyano-4-pyrimidinyl |
| 5-trifluoromethyl-4-pyrimidinyl |
| 4-trifluoromethyl-3-pyridazinyl |
| 4-cyano-3-pyridazinyl |
| 4-nitro-2-pyridazinyl |
| 4-methoxy-3-pyridazinyl |
| 3-trifluoromethyl-2-pyrazinyl |
| 3-cyano-2-pyrazinyl |
| 3-nitro-2-pyrazinyl |
| 3-methoxy-2-pyrazinyl |

Examples of plant diseases on which the compound of the present invention manifests a controlling effect include the following diseases.

Rice plant: *Magnaporthe grisea, Cochliobolus miyabeanus, Rhizoctonia solani;*

Wheat and baley: *Erysiphe graminis, Fusarium graminearum, F. avenacerum, F. Culmorum, Puccinia striiformis, P. graminis, P. recondita, P. hordei, Typhula* sp., *Micronectriella nivalis, Ustilago tritici, U. Nuda, Tilletia caries, Pseudocercosporella herpotrichoides, Rhynchosporium secalis, Septoria tritici; Leptosphaeria nodorum;*

Citrus: *Diaporthe citri, Elsinoe fawcetti, Penicillium digitatum, P. Italicum;*

Apple: *Monilinia mali, Valsa ceratosperma, Podosphaera leucotricha, Alternaria alternata* apple pathotype, *Venturia inaequalis;*

Pear: *Venturia nashicola, V. Pirina, Alternaria alternata* Japanese pear pathotype, *Gymnosporangium haraeanum;*

Peach: *Monilinia fructicola, Cladosporium carpophilum, Phomopsis* sp.;

Grape: *Elsinoe ampelina, Glomerella cingulata, Uncinula necator, Phakopsora ampelopsidis, Guignardia bidwellii, Plasmopara viticola;*

Persimmon: *Gloeosporium kaki, Cercospora kaki, Mycosphaerella nawae;*

Cucurbit: *Colletotrichum lagenarium, Sphaerotheca fuliginea, Mycosphaerella melonis, Fusarium oxysporum, Pseudoperonospora cubensis, Phytophthora* sp.; *Pythium* sp.;

Tomato: *Alternaria solani, Cladosporium fulvum, Phytophthora infestans;*

Eggplant: *Phomopsis vexans, Erysiphe cichoracearum;*

Cruciferae vegetables: *Alternaria japonica, Cercosporella brassicae;*

Green onion: *Puccinia allii;*

Soybean: *Cercospora kikuchii, Elsinoe glycines, Diaporthe phaseolorum* var. *sojae, Phakopsora pachyrhizi;*

Kidney bean: *Colletotrichum lindemthianum;*

Peanut: *Cercospora personata, Cercospora arachidicola;*

Pea: *Erysiphe pisi;*

Potato: *Alternaria solani, Phytophthora infestans;*

Strawberry: *Sphaerotheca humuli;*

Tea: *Exobasidium reticulatum, Elsinoe leucospila;*

Tobacco: *Alternaria longipes, Erysiphe cichoracearum, Colletotrichum tabacum, Peronospora tabacina; Phytophthora nicotianae;*

Sugar beet: *Cercospora beticola;*

Rose: *Diplocarpon rosae, Sphaerotheca pannosa;*

Chrysanthemum: *Septoria chrysanthemi-indici), Puccinia horiana;*

Various crops: *Botrytis cinerea, Sclerotinia sclerotiorum;*

Radish: *Alternaria brassicicola;*

Turf: *Sclerotinia homeocarpa, Rhizoctonia solani.*

By applying a compound of the present invention as it is to a plant or soil, a fungicidal effect is manifested. Usually, however, a composition containing a compound of the present invention and a carrier is used. That is, for obtaining the fungicide of the present invention, a compound of the present invention and a solid carrier and/or liquid carrier are mixed, and if necessary, a surfactant and other auxiliary substances for formulation are added, and the mixture is formulated into an emulsifiable concentrate, wettable powder, water dispersible granule, flowable agent, dust, granule and the like.

These formulations contain a compound of the present invention in an amount of usually 0.1 to 90 wt %.

Examples of the solid carrier to be used in formulating include fine powdery or granular materials composed of minerals such as kaolin clay, attapulgite clay, bentonite, montmorillonite, acid clay, pyrophyllite, talc, diatomaceous earth, calcite and the like, natural organic materials such as corn cob powder, walnut shell powder and the like, synthetic organic materials such as urea and the like, salts such as calcium carbonate, ammonium sulfate and the like, synthetic inorganic materials such as synthetic hydrated silica and the like, and examples of the liquid carrier include aromatic hydrocarbons such as xylene, alkylbenzene, methylnaphthalene and the like, alcohols such as 2-propanol, ethylene glycol, propylene glycol, cellosolve and the like, ketones such as acetone, cyclohexanone, isophorone and the like, vegetable oils such as soy bean oil, cotton seed oil and the like, aliphatic hydrocarbons, esters, dimethyl sulfoxide, acetonitrile, and water.

Examples of the surfactant include anionic surfactants such as alkyl sulfate salts, alkylarylsulfononic acid salts, dialkylsulfosuccinic acid salts, polyoxyethylene alkyl aryl ether phosphate salts, ligninsulfonic acid salts, naphthalene sulfonate-formaldehyde polycondensate and the like, and nonionic surfactants such as polyoxyethylene alkyl aryl ethers, polyoxyethylene alkyl polyoxypropylene block copolymers, sorbitan fatty esters, and the like.

Examples of other auxiliary substances for formulation include water-soluble polymers such as polyvinyl alcohol, polyvinyl pyrrolidone and the like, gum Arabic, alginic acid and salts thereof, polysaccharides such as CMC (carboxymethylcellulose), xanthan gum and the like, inorganic substances such as aluminum magnesium silicate, alumina sol and the like, preservatives, coloring agents and, stabilizers such as PAP (acidic isopropyl phosphate), BHT and the like.

By treating a plant body with the fungicide of the present invention, the plant can be protected from plant diseases. By treating soil with the fungicide of the present invention, a plant growing in the soil can be protected from plant diseases. That is, the fungicide of the present invention is used in a plant disease controlling method having a process of applying usually an effective amount of a fungicide of the present invention to a plant or soil in which a plant is grown.

When the fungicide of the present invention is used to treat a plant body or when the fungicide of the present invention is used to treat soil, the treating amount thereof can vary depending on the kind of a crop as a controlling subject plant, the kind of a controlling subject disease, the generation extent of a controlling subject disease, formulation form, treatment period, weather conditions and the like, and it is usually 1 to 5000 g, preferably 5 to 1000 g in terms of a compound of the present invention per 10000 m².

An emulsifiable concentrate, wettable powder, flowable agent and the like are usually diluted with water and sprayed for treatment. In this case, the concentration of a compound of the present invention is usually in the range of 0.0001 to 3 wt %, preferably 0.0005 to 1 wt %. A dust, granule and the like are usually used for treatment without diluting.

The fungicide of the present invention can also be used for sterilization of seeds. The sterilization method includes, for example, a method in which plant seeds are immersed in a fungicide of the present invention wherein the concentration of a compound of the present invention is regulated to 1 to 1000 ppm, a method in which a fungicide of the present invention wherein the concentration of a compound of the present invention is regulated to 1 to 1000 ppm is sprayed or painted on plant seeds, and a method in which a fungicide of the present invention formulated into a dust is coated on plant seeds.

The plant disease controlling method of the present invention is usually carried out by treating a plant or soil in which a plant is grown on which generation of a disease is prospected, with an effective amount of a fungicide of the present invention.

The fungicide of the present invention is used usually as a fungicide for agriculture and horticulture, namely, as a fungicide for controlling plant diseases in plowed field, paddy field, orchard, tea field, pasture, turf land and the like.

The fungicide of the present invention can also be used together with other fungicide, insecticides, acaricide, nematicide, herbicide, plant growth regulator and/or fertilizer.

Examples of active ingredients of such fungicides include azole type fungicidal compounds such as propiconazole, prothioconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil and flutriafol and the like; cyclic amine type fungicidal compounds such as fenpropimorph, tridemorph, fenpropidin and the like; benzimidazole type fungicidal compounds such as carbendazim, benomyl, thiabendazole, thiophanate-methyl and the like; procymidone; cyprodinyl; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; picoxystrobin; pyraclostrobin; N-methyl-α-methoximino-2-((2,5-dimethylphenoxy)methyl)phenyl acetamide; spiroxamine; quinoxyfen; fenhexamide; famoxadone; fenamidone; iprovalicarb; benthiavalicarb; cyazofamid; boscalid; metrafenone and cyflufenamid.

The present invention will be described further in detail by production examples, formulation examples and test examples and the like below, but the present invention is not limited to these examples.

First, production examples of compounds of the present invention are shown.

PRODUCTION EXAMPLE 1

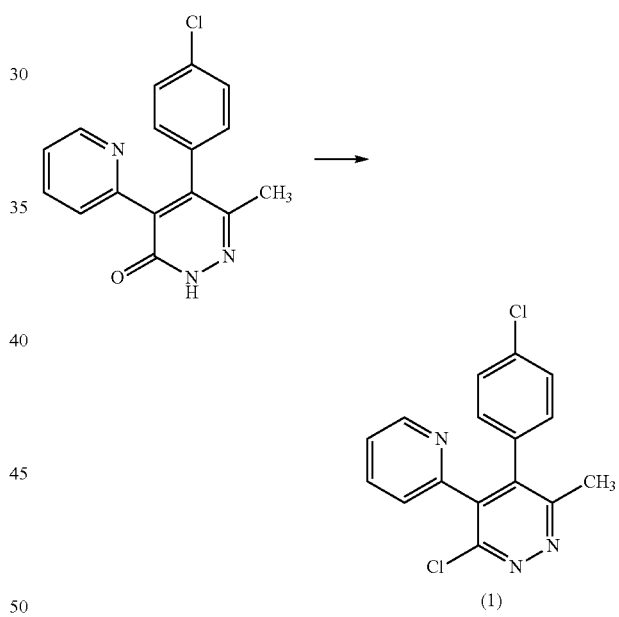

(1)

0.24 g of 5-(4-chlorophenyl)-6-methyl-4-(2-pyridyl)-2H-pyridazin-3-one and 3 g phosphorus oxychloride were mixed. The mixture was stirred for 1 hour on an oil bath of 110° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure to obtain 0.25 g 3-chloro-5-(4-chlorophenyl)-6-methyl-4-(2-pyridyl)pyridazine (hereinafter, described as compound (1) of the present invention.).

Compound (1) of the Present Invention $^1$H-NMR (CDCl$_3$, TMS) δ (ppm): 2.55 (3H, s), 7.00 (2H, d, J=8.6 Hz), 7.06 (1H, d, J=7.8 Hz), 7.25 (2H, d, J=8.6 Hz), 7.17-7.25 (1H, m), 7.61 (1H, dt, J=1.8, 7.8 Hz), 8.56 (1H, d, J=4.2 Hz)

PRODUCTION EXAMPLE 2

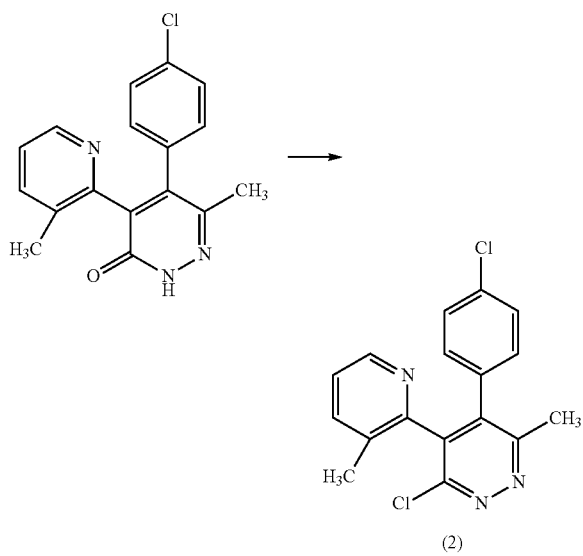

0.34 g of 5-(4-chlorophenyl)-6-methyl-4-(3-methyl-2-pyridyl)-2H-pyridazin-3-one and 3.6 g of phosphorus oxychloride were mixed. The mixture was stirred for 2 hours on an oil bath of 120° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.33 g of the resultant residue was subjected to silica gel column chromatograph, to obtain 0.21 g of 3-chloro-5-(4-chlorophenyl)-6-methyl-4-(3-methyl-2-pyridyl)pyridazine (hereinafter, described as compound (2) of the present invention.).

Compound (2) of the Present Invention $^1$H-NMR (CDCl$_3$, TMS) δ (ppm): 1.98 (3H, s), 2.56 (3H, s), 7.04 (2H, br d, J=8.8 Hz), 7.15 (1H, m), 7.23 (2H, d, J=8.8 Hz), 7.43 (1H, d, J=7.8 z), 8.42 (1H, d, J=3.6 Hz)

PRODUCTION EXAMPLE 3

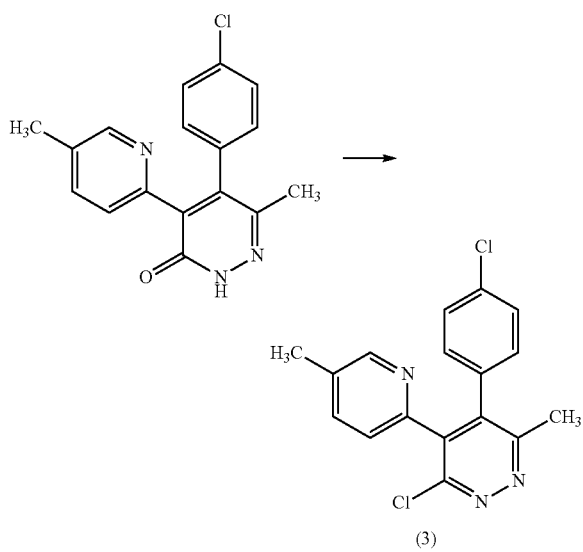

0.20 g of 5-(4-chlorophenyl)-6-methyl-4-(5-methyl-2-pyridyl)-2H-pyridazin-3-one and 3.2 g of phosphorus oxychloride were mixed. The mixture was stirred for 2 hours on an oil bath of 120° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.20 g of the resultant residue was subjected to silica gel column chromatography, to obtain 0.18 g of 3-chloro-5-(4-chlorophenyl)-6-methyl-4-(5-methyl-2-pyridyl)pyridazine (hereinafter, described as compound (3) of the present invention.).

Compound (3) of the Present Invention $^1$H-NMR (CDCl$_3$, TMS) δ (ppm): 2.32 (3H, s), 2.53 (3H, s), 6.94 (1H, d, J=7.8 z), 7.00 (2H, d, J=8.4 Hz), 7.25 (2H, d, J=8.4 Hz), 7.40 (1H, d, J=7.8 z), 8.38 (1H, s)

PRODUCTION EXAMPLE 4

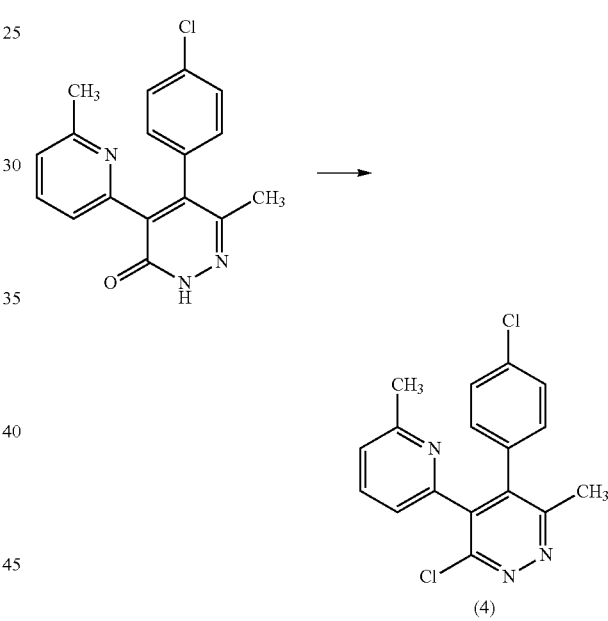

6 g of 5-(4-chlorophenyl)-6-methyl-4-(6-methyl-2-pyridyl)-2H-pyridazin-3-one and 2 g of phosphorus oxychloride were mixed. The mixture was stirred for 4 hours on an oil bath of 130° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure, to obtain 4 mg of 3-chloro-5-(4-chlorophenyl)-6-methyl-4-(6-methyl-2-pyridyl)pyridazine (hereinafter, described as compound (4) of the present invention.).

Compound (4) of the Present Invention $^1$H-NMR (CDCl$_3$, TMS) δ (ppm): 2.47 (3H, s), 2.53 (3H, s), 6.89 (1H, d, J=7.8 Hz), 7.01 (2H, d, J=8.4 Hz), 7.05 (1H, d, J=7.8 Hz), 7.25 (2H, d, J=8.4 Hz), 7.50 (1H, t, J=7.8 Hz)

PRODUCTION EXAMPLE 5

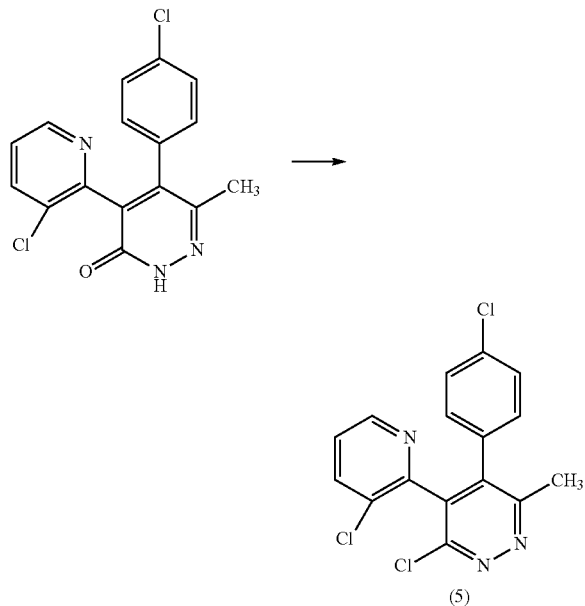

0.64 g of 5-(4-chlorophenyl)-4-(3-chloro-2-pyridyl)-6-methyl-2H-pyridazin-3-one and 15 g of phosphorus oxychloride were mixed. The mixture was stirred for 6 hours under reflux with heating. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.67 g of the resultant residue was subjected to silica gel column chromatography, to obtain 0.50 g of 3-chloro-5-(4-chlorophenyl)-4-(3-chloro-2-pyridyl)-6-methylpyridazine (hereinafter, described as compound (5) of the present invention.).

Compound (5) of the Present Invention $^1$H-NMR (CDCl$_3$, TMS) δ (ppm): 2.56 (3H, s), 7.08 (2H, d, J=8.8 Hz), 7.20-7.25 (3H), 7.66 (1H, dd, J=8.3, 1.5 Hz), 8.47 (1H, dd, J=4.6, 1.5 Hz)

PRODUCTION EXAMPLE 6

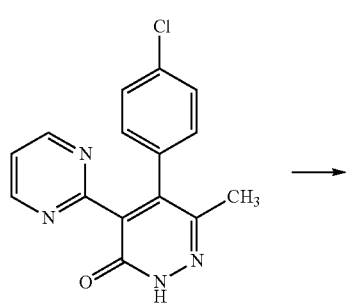

0.64 g of 5-(4-chlorophenyl)-6-methyl-4-(2-pyrimidinyl)-2H-pyridazin-3-one and 10.4 g of phosphorus oxychloride were mixed. The mixture was stirred for 2 hours under reflux with heating. The reaction mixture was allowed to cool to room temperature, then, concentrated under reduced pressure. To the resultant residue was added ethyl acetate and ice-cooled sodium bicarbonate water was added. The mixture was stirred for about 5 minutes at room temperature, then, liquid-separated. The organic layer was washed with brine, and dried over anhydrous magnesium sulfate, then, concentrated under reduced pressure. 0.56 g of the resultant residue was subjected to silica gel column chromatography, to obtain 0.49 g of 3-chloro-5-(4-chlorophenyl)-6-methyl-4-(2-pyrimidinyl)pyridazine (hereinafter, described as compound (6) of the present invention (6).).

Compound (6) of the Present Invention $^1$H-NMR (CDCl$_3$, TMS) δ (ppm): 2.57 (3H, s), 7.06 (2H, d, J=8.8 Hz), 7.21 (1H, t, J=4.9 Hz), 7.26 (2H, d, J=8.8 Hz), 8.70 (1H, d, J=4.9 Hz)

PRODUCTION EXAMPLE 7

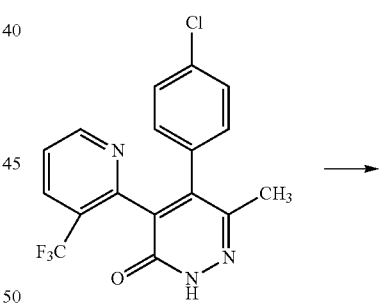

0.69 g of 5-(4-chlorophenyl)-6-methyl-4-(3-trifluoromethyl-2-pyridyl)-2H-pyridazin-3-one and 6.3 g of phosphorus oxychloride were mixed. The mixture was stirred for 2 hours under reflux with heating. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.50 g of the resultant residue was subjected to silica gel column chromatography, to obtain 0.11 g of 3-chloro-5-(4-chlorophenyl)-6-methyl-4-(3-trifluoromethyl-2-pyridyl)pyridazine (hereinafter, described as compound (7) of the present invention.).

Compound (7) of the Present Invention
¹H-NMR (CDCl₃, TMS) δ (ppm): 2.55 (3H, s), 7.05 (2H, d, J=8.6 Hz), 7.22 (2H, br), 7.41-7.44 (1H, m), 7.93 (1H, dd, J=8.3, 1.0 Hz), 8.80 (1H, dd, J=4.9, 1.0 Hz)

PRODUCTION EXAMPLE 8

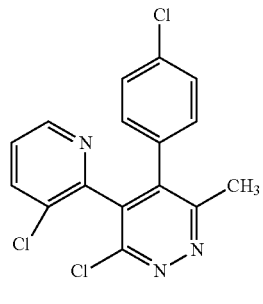

(5)

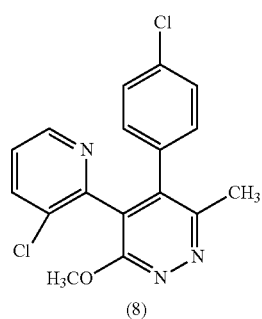

(8)

0.35 g of the compound (5) of the present invention, 1.92 g of sodium methoxide (28% methanol solution) and 6 ml of anhydrous methanol were mixed, then, the mixture was stirred for 2 hours under reflux with heating. The reaction mixture was allowed to cool to room temperature, then, ice water was added, and extracted with ethyl acetate. The organic layer was washed with brine twice, and dried over anhydrous magnesium sulfate, then, concentrated under reduced pressure, to obtain 0.34 g of 5-(4-chlorophenyl)-4-(3-chloro-2-pyridyl)-3-methoxy-6-methyl pyridazine (hereinafter, described as compound (8) of the present invention.).

Compound (8) of the Present Invention
¹H-NMR (CDCl₃, TMS) δ (ppm): 2.46 (3H, s), 4.10 (3H, s), 7.08 (2H), 7.1-7.3 (3H), 7.62 (1H), 8.42 (1H)

PRODUCTION EXAMPLE 9

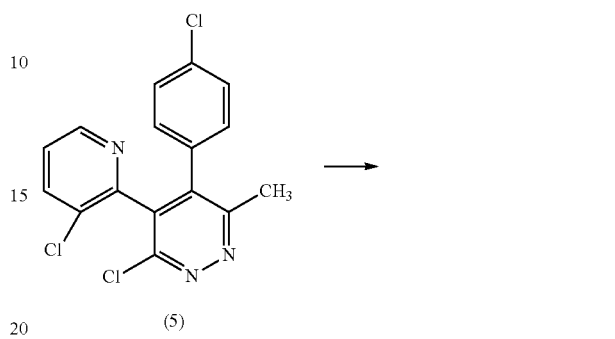

(5)

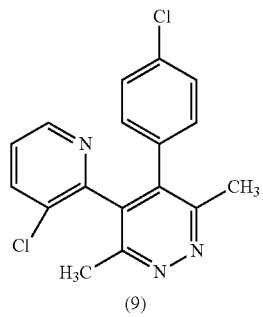

(9)

0.48 g of sodium hydride (55% oil dispersion) was added to 5 ml of N,N-dimethylformamide. Into this, 1.76 g of diethyl malonate was added dropwise under a nitrogen atmosphere, and the mixture was stirred at room temperature for 30 minutes. To this was added 1.05 g of the compound (5) of the present invention, and the mixture was stirred at 100° C. for 16 hours, and at 120° C. for 9.5 hours. The reaction mixture was allowed to cool to room temperature, then, ice water was added, and extracted with ethyl acetate. The organic layer was washed with brine three times, and dried over anhydrous magnesium sulfate, then, concentrated under reduced pressure. 1.45 g of the resultant residue was subjected to silica gel column chromatography to obtain 0.23 g of solid. This solid was subjected to preparative thin layer silica gel chromatography to obtain 0.15 g of an intermediate. The resultant intermediate and 3 ml of concentrated hydrochloric acid were mixed. The mixture was stirred for 30 minutes on an oil bath of 100° C. The reaction mixture was allowed to cool to room temperature, then, added to a mixture of ice and 10% sodium hydroxide aqueous solution, and the mixture was extracted with ethyl acetate. The organic layer was washed with brine twice, and dried over anhydrous magnesium sulfate, then, concentrated under reduced pressure. 0.07 g of the resultant residue was subjected to silica gel column chromatography, to obtain 0.05 g of 5-(4-chlorophenyl)-4-(3-chloro-2-pyridyl)-3,6-dimethylpyridazine (hereinafter, described as compound (9) of the present invention.).

Compound (9) of the Present Invention
¹H-NMR (CDCl₃, TMS) δ (ppm): 2.44 (3H, s), 2.54 (3H, s), 7.05 (2H, br), 7.15-7.3 (3H), 7.63 (1H, dd, J=8.0, 1.5 Hz), 8.47 (1H, dd, J=4.6, 1.5 Hz)

PRODUCTION EXAMPLE 10

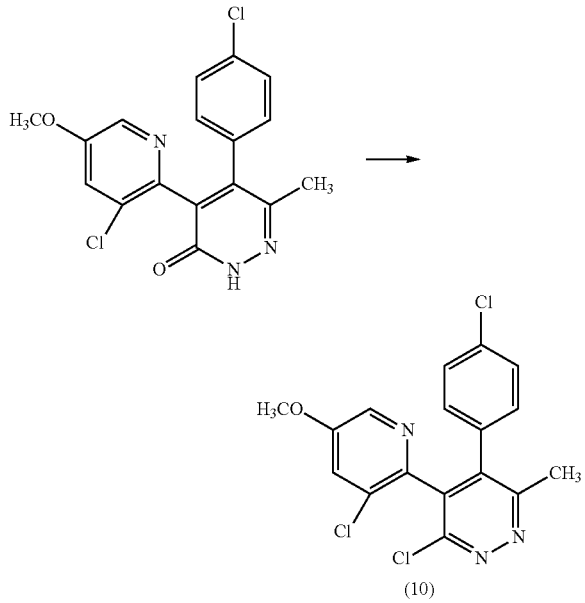

(10)

0.24 g of 5-(4-chlorophenyl)-4-(3-chloro-5-methoxy-2-pyridyl)-6-methyl-2H-pyridazin-3-one and 6 g of phosphorus oxychloride were mixed. The mixture was stirred for 2 hours on an oil bath of 110° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.12 g of the resultant residue was subjected to silica gel column chromatography, to obtain 0.07 g of 3-chloro-5-(4-chlorophenyl)-4-(3-chloro-5-methoxy-2-pyridyl)-6-methylpyridazine (hereinafter, described as compound (10) of the present invention.).

Compound (10) of the Present Invention
¹H-NMR (CDCl₃, TMS) δ (ppm): 2.55 (3H, s), 3.86 (3H, s), 7.07 (2H, d, J=8.8 Hz), 7.15 (1H, d, J=2.7 Hz), 7.27 (2H, d, J=8.8 Hz), 8.15 (1H, d, J=2.7 Hz)

PRODUCTION EXAMPLE 11

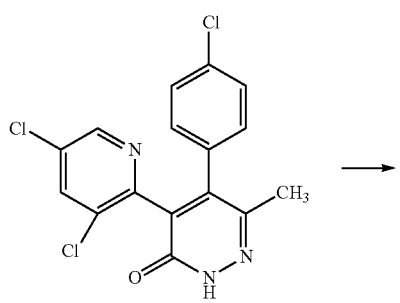

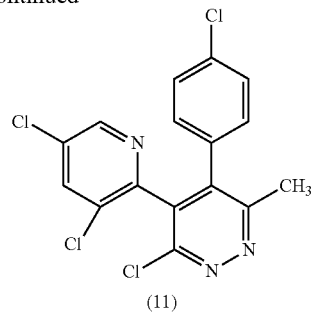

(11)

0.66 g of 5-(4-chlorophenyl)-4-(3,5-dichloro-2-pyridyl)-6-methyl-2H-pyridazin-3-one and 6 g of phosphorus oxychloride were mixed. The mixture was stirred for 2 hours on an oil bath of 110° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.67 g of the resultant residue was subjected to silica gel column chromatography, to obtain 0.47 g of 3-chloro-5-(4-chlorophenyl)-4-(3,5-dichloro-2-pyridyl)-6-methylpyridazine (hereinafter, described as compound (11) of the present invention.).

Compound (11) of the Present Invention
¹H-NMR (CDCl₃, TMS) δ (ppm): 2.56 (3H, s), 7.06 (2H, d, J=7.8 Hz), 7.29 (2H, d, J=7.8 Hz), 7.69 (1H, s), 8.42 (1H, s)

PRODUCTION EXAMPLE 12

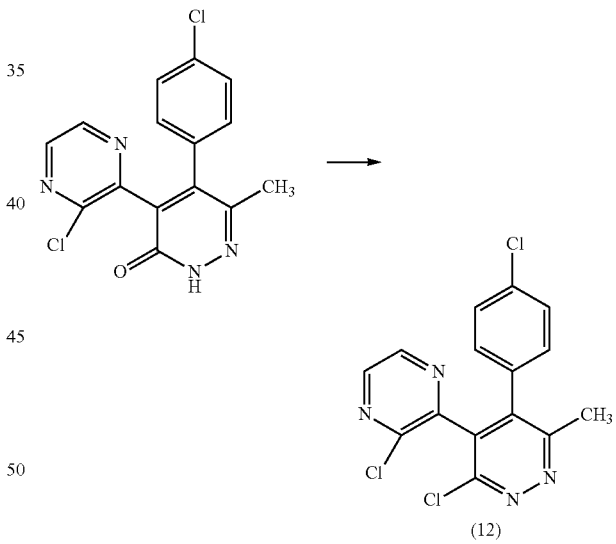

(12)

0.57 g of 5-(4-chlorophenyl)-4-(3-chloro-2-pyrazinyl)-6-methyl-2H-pyridazin-3-one and 6 g of phosphorus oxychloride were mixed. The mixture was stirred for 2 hours on an oil bath of 110° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.60 g of the resultant residue was subjected to silica gel column chromatography, to obtain 0.49 g of 3-chloro-5-(4-chlorophenyl)-4-(3-chloro-2-pyrazinyl)-6-methylpyridazine (hereinafter, described as compound (12) of the present invention.).

Compound (12) of the Present Invention $^1$H-NMR (CDCl$_3$, TMS) δ (ppm): 2.58 (3H, s), 7.08 (2H, br), 7.29 (2H, d, J=8.6 Hz), 8.34 (1H, d, J=2.4 Hz), 8.48 (1H, d, J=2.4 Hz)

PRODUCTION EXAMPLE 13

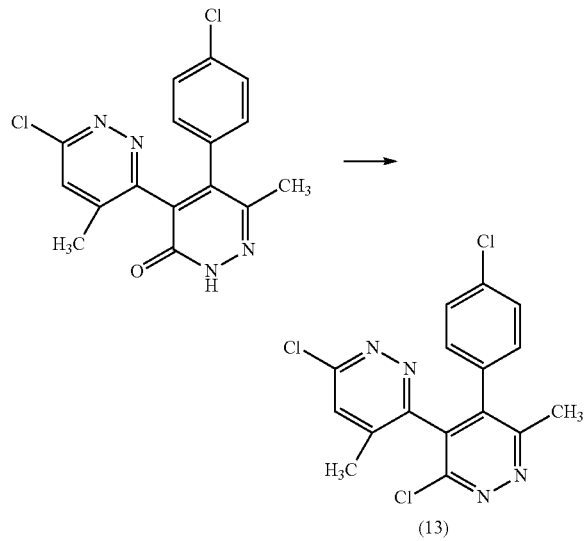

0.30 g of 5-(4-chlorophenyl)-4-(6-chloro-4-methyl-3-pyridazinyl)-6-methyl-2H-pyridazin-3-one and 5 g of phosphorus oxychloride were mixed. The mixture was stirred for 1.5 hours on an oil bath of 110° C. The reaction mixture was allowed to cool to room temperature, the, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.31 g of the resultant residue was subjected to silica gel column chromatography, to obtain 0.26 g of 3-chloro-5-(4-chlorophenyl)-4-(6-chloro-4-methyl-3-pyridazin yl)-6-methylpyridazine (hereinafter, described as compound (13) of the present invention (13).).

Compound (13) of the Present Invention
$^1$H-NMR (CDCl$_3$, TMS) δ (ppm): 2.04 (3H, s), 2.59 (3H, s), 6.9-7.2 (2H, br), 7.25-7.35 (3H)

PRODUCTION EXAMPLE 14

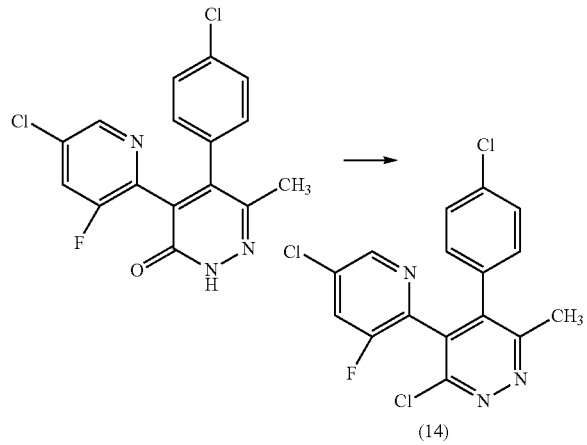

0.3 g of 5-(4-chlorophenyl)-4-(5-chloro-3-fluoro-2-pyridyl)-6-methyl-2H-pyridazin-3-one and 10 g of phosphorus oxychloride were mixed. The mixture was stirred for 1.5 hours on an oil bath of 110° C. The reaction mixture was allowed to cool to room temperature, the, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.3 g of the resultant residue was subjected to silica gel column chromatography, to obtain 0.22 g of 3-chloro-5-(4-chlorophenyl)-4-(5-chloro-3-fluoro-2-pyridyl)-6-methylpyridazine (hereinafter, described as compound (14) of the present invention.).

Compound (14) of the Present Invention
$^1$H-NMR (CDCl$_3$, TMS) δ (ppm): 2.56 (3H, s), 7.03 (2H, d, J=8.5 Hz), 7.29 (2H, d, J=8.5 Hz), 7.41 (1H, dd, J=8.5, 2.0 Hz), 8.37 (1H, dd, J=2.0, 1.0 Hz)

PRODUCTION EXAMPLE 15

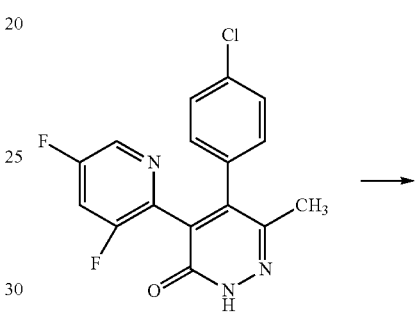

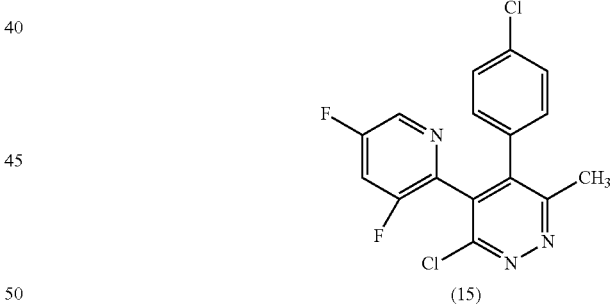

0.14 g of 5-(4-chlorophenyl)-4-(3,5-difluoro-2-pyridyl)-6-methyl-2H-pyridazin-3-one and 5 g of phosphorus oxychloride were mixed. The mixture was stirred for 1.5 hours on an oil bath of 120° C. The reaction mixture was allowed to cool to room temperature, the, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.14 g of the resultant residue was subjected to silica gel column chromatography, to obtain 0.08 g of 3-chloro-5-(4-chlorophenyl)-4-(3,5-difluoro-2-pyridyl)-6-methylpyridazine (hereinafter, described as compound (15) of the present invention.).

Compound (15) of the Present Invention

¹H-NMR (CDCl₃, TMS) δ (ppm): 2.56 (3H, s), 7.02 (2H, d, J=8.8 Hz), 7.16 (1H, m), 7.29 (2H, d, J=8.8 Hz), 8.31 (1H, d, J=2.2 Hz)

PRODUCTION EXAMPLE 16

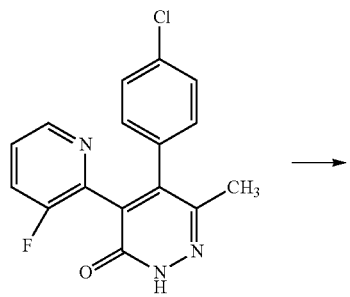

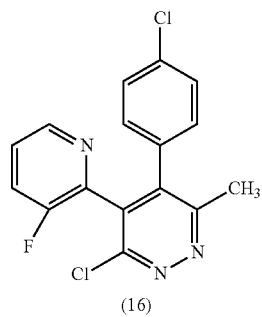

0.63 g of 5-(4-chlorophenyl)-4-(3-fluoro-2-pyridyl)-6-methyl-2H-pyridazin-3-one and 7.2 g of phosphorus oxychloride were mixed. The mixture was stirred for 1.5 hours on an oil bath of 120° C. The reaction mixture was allowed to cool to room temperature, then, concentrated under reduced pressure. To the resultant residue were added ethyl acetate and ice-cooled sodium bicarbonate water. The mixture was stirred for about 5 minutes at room temperature, then, liquid-separated. The organic layer was washed with brine, and dried over anhydrous magnesium sulfate, then, concentrated under reduced pressure. 0.64 g of the resultant residue was subjected to silica gel column chromatography, to obtain 0.51 g of 3-chloro-5-(4-chlorophenyl)-4-(3-fluoro-2-pyridyl)-6-methylpyridazine (hereinafter, described as compound (16) of the present invention.).

Compound (16) of the Present Invention

¹H-NMR (CDCl₃, TMS) δ (ppm): 2.56 (3H, s), 7.04 (2H, d, J=8.8 Hz), 7.2-7.4 (4H), 8.39 (1H, m), Next, examples for producing an intermediate of a compound of the present invention are shown as reference production examples.

REFERENCE PRODUCTION EXAMPLE 1

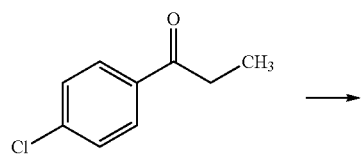

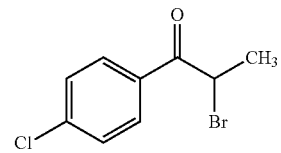

A mixture of 10.12 g of 4'-chloropropiophenone, 0.1 ml of hydrobromic acid (48% aqueous solution) and 60 ml of acetic acid was cooled to 0° C. under a nitrogen atmosphere. 3.1 ml of bromine was added dropwise into the mixture, then, the mixture was allowed to warm to room temperature and stirred for 1 hour. The reaction mixture was concentrated under reduced pressure to obtain 14.34 g of 2-bromo-4'-chloropropiophenone.

¹H-NMR (CDCl₃, TMS) δ (ppm): 1.90 (3H, d, J=6.5 Hz), 5.22 (1H, q, J=6.5 Hz), 7.46 (2H, d, J=8.7 Hz), 7.97 (2H, d, J=8.7 Hz)

REFERENCE PRODUCTION EXAMPLE 2

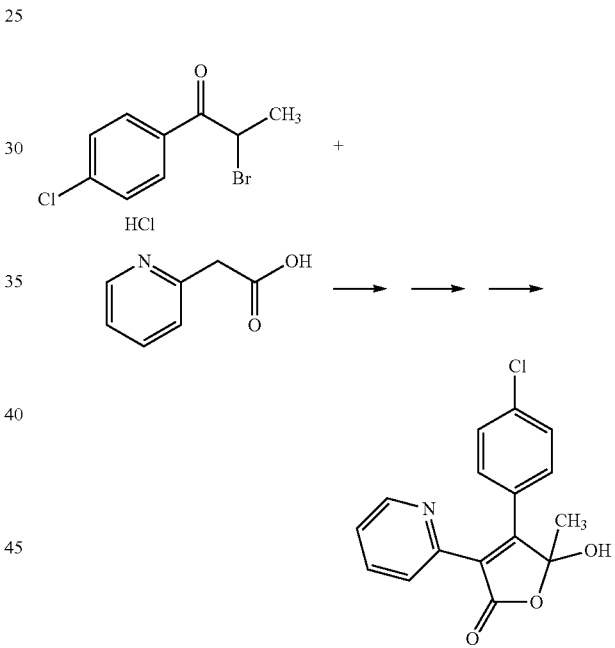

To a mixture was 1.05 g of 2-bromo-4'-chloropropiophenone, 0.74 g of 2-pyridylacetic acid.hydrochloride and 20 ml of acetonitrile was added 1.07 g of triethylamine. The mixture was stirred overnight at room temperature. Thereafter, the mixture was cooled to 0° C., and into this was added dropwise 2.58 g of DBU, and the mixture was stirred for 2 hours at the same temperature. Then, the mixture was stirred for 5 hours at room temperature while blowing air into the reaction mixture. To the reaction mixture was added 8 ml of 1.2 mol/L hydrochloric acid, and extracted with ethyl acetate. The organic layer was washed with saturated brine twice, and dried over anhydrous magnesium sulfate, then, concentrated under reduced pressure. 1.14 g of the resultant residue was subjected to silica gel column chromatography, to obtain 0.79 g of 4-(4-chlorophenyl)-5-hydroxy-5-methyl-3-(2-pyridyl)-2(5H)-furanone.

¹H-NMR (CDCl₃, TMS) δ (ppm): 1.68 (3H, s), 5.52 (1H, br), 7.28 (2H, d, J=8.8 Hz), 7.25-7.31 (1H, m), 7.41 (2H, d, J=8.8 Hz), 7.55 (1H, d, J=7.8 Hz), 7.75 (1H, dt, J=1.7, 7.8 Hz), 8.51 (1H, d, J=3.9 Hz)

REFERENCE PRODUCTION EXAMPLE 3

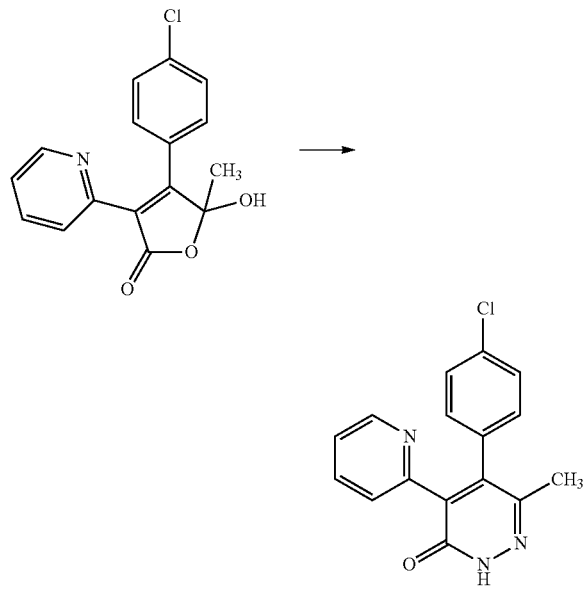 [SMILES: CC1(O)OC(=O)C(c2ccccn2)=C1c1ccc(Cl)cc1 ; Cc1n[nH]c(=O)c(-c2ccccn2)c1-c1ccc(Cl)cc1]

A mixture of 0.67 g of 4-(4-chlorophenyl)-5-hydroxy-5-methyl-3-(2-pyridyl)-2(5H)-furanone, 0.25 g of hydrazine monohydrate and 8 ml of 1-butanol was stirred for 5 hours on an oil bath of 110° C. The reaction mixture was cooled to 0° C. The deposited solid was collected by filtration. The resultant solid was washed with a mixed solvent of hexane and t-butyl methyl ether, and dried under reduced pressure, to obtain 0.32 g of 5-(4-chlorophenyl)-6-methyl-4-(2-pyridyl)-2H-pyridazin-3-one.

¹H-NMR (CDCl₃+DMSO-d₆, TMS) δ (ppm): 2.11 (3H, s), 7.01 (2H, d, J=8.3 Hz), 7.08-7.13 (1H, m), 7.22 (2H, d, J=8.3 Hz), 7.2-7.25 (1H, m), 7.57 (1H, dt, J=1.7, 7.7 Hz), 8.45 (1H, d, J=4.9 Hz)

REFERENCE PRODUCTION EXAMPLE 4

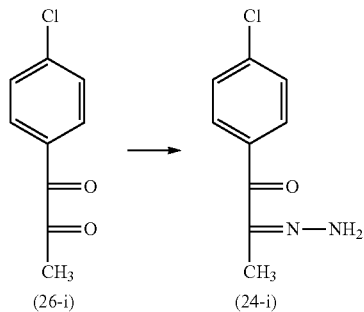

21.90 g of a compound of the formula (26-i) was dissolved in 100 ml of ethanol, and a solution prepared by dissolving 6.00 g of hydrazine monohydrate in 20 ml of ethanol was added dropwise into this under a nitrogen atmosphere while cooling with ice. The mixture was stirred for 1 hour at the same temperature, and stirred for 2 hours at room temperature, then, allowed to stand overnight. To the reaction mixture was added 80 ml of chloroform, the mixture was filtrated, and the resultant filtrate was concentrated under reduce pressure, to obtain 23.52 g of a compound of the formula (24-i).

¹H-NMR (CDCl₃, TMS) δ (ppm): 2.05 (3H, s), 6.09 (2H, br s), 7.38 (2H, d, J=8 Hz), 7.81 (2H, d, J=8 Hz)

REFERENCE PRODUCTION EXAMPLE 5

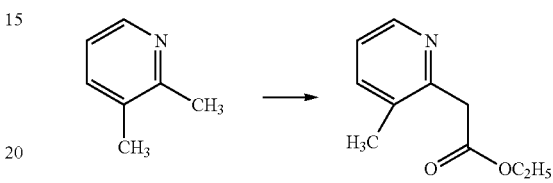

To a mixture of 10.72 g of 2,3-lutidine and 150 ml of tetrahydrofuran was added 63 ml of n-butyllithium (1.6 mol/L hexane solution) at room temperature. Into the mixture, a mixture of 11.81 g of diethyl carbonate and 50 ml of anhydrous tetrahydrofuran was added dropwise at −70° C. The mixture was heated up to room temperature. The reaction mixture was added to ice-cooled ammonium chloride aqueous solution, and extracted with tert-butyl methyl ether. The organic layer was washed with saturated brine, and dried over anhydrous magnesium sulfate, then, concentrated under reduced pressure. 16.16 g of the resultant residue was subjected to silica gel column chromatography, to obtain 6.31 g of ethyl (3-methyl-2-pyridyl)acetate.

¹H-NMR (CDCl₃, TMS) δ (ppm): 1.25 (3H, t, J=7.2 Hz), 2.31 (3H, s), 3.87 (2H, s), 4.18 (2H, q, J=7.2 Hz), 7.10 (1H, m), 7.47 (1H, dd, J=1.2, 7.7 Hz), 8.39 (1H, dd, J=1.2, 4.9 Hz)

The following compounds were produced according to Reference Production Example 5.

Ethyl (5-methyl-2-pyridyl)acetate
¹H-NMR (CDCl₃, TMS) δ (ppm): 1.26 (3H, t, J=7.2 Hz), 2.32 (3H, s), 3.80 (2H, s), 4.18 (2H, q, J=7.2 Hz), 7.19 (1H, d, J=7.8 Hz), 7.46 (1H, dd, J=2.2, 7.8 Hz), 8.38 (1H, d, J=2.2 Hz)

Ethyl (6-methyl-2-pyridyl)acetate
¹H-NMR (CDCl₃, TMS) δ (ppm): 1.26 (3H, t, J=7.3 Hz), 2.54 (3H, s), 3.81 (2H, s), 4.18 (2H, q, J=7.3 Hz), 7.04 (1H, d, J=7.8 Hz), 7.09 (1H, d, J=7.8 Hz), 7.54 (1H, t, J=7.8 Hz)

REFERENCE PRODUCTION EXAMPLE 6

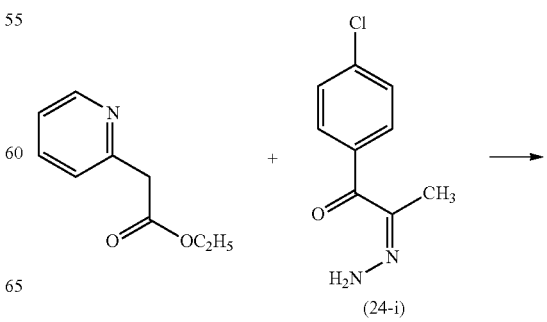

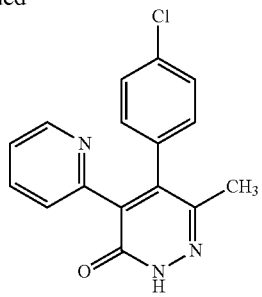

1.97 g of a compound of the formula (24-i), 1.65 g of ethyl 2-pyridyl acetate, 3.40 g of sodium ethoxide (20% ethanol solution) and 35 ml ethanol were mixed. The mixture was stirred for 5 hours under reflux with heating. The reaction mixture was allowed to cool to room temperature, then, to the reaction mixture was added ice and 8.3 ml of 1.2 mol/L hydrochloric acid sequentially, and extracted with ethyl acetate. The organic layer was washed with saturated brine, and dried over anhydrous magnesium sulfate, then, concentrated under reduced pressure. 2.52 g of the resultant residue was subjected to silica gel column chromatography, to obtain 0.70 g of 5-(4-chlorophenyl)-6-methyl-4-(2-pyridyl)-2H-pyridazin-3-one The following compounds were produced according to Reference Production Example 6.

5-(4-chlorophenyl)-6-methyl-4-(3-methyl-2-pyridyl)-2H-pyridazin-3-one $^1$H-NMR (CDCl$_3$, TMS) δ (ppm): 2.12 (3H, s), 2.13 (3H, s), 7.06 (1H, m), 7.1-7.3 (4H, m), 7.39 (1H, d, J=7.8 Hz), 8.34 (1H, d, J=3.7 Hz), 11.61 (1H, brs)

5-(4-chlorophenyl)-6-methyl-4-(5-methyl-2-pyridyl)-2H-pyridazin-3-one $^1$H-NMR (CDCl$_3$, TMS) δ (ppm): 2.10 (3H, s), 2.26 (3H, s), 7.0-7.05 (2H, m), 7.13 (2H, d, J=7.2 Hz), 7.20-7.25 (2H, m), 7.38 (1H, d, J=7.2 Hz), 8.29 (1H, s)

5-(4-chlorophenyl)-6-methyl-4-(6-methyl-2-pyridyl)-2H-pyridazin-3-one $^1$H-NMR (CDCl$_3$, TMS) δ (ppm): 2.11 (3H, s), 2.36 (3H, s), 6.96 (1H, d, J=7.8 Hz), 7.03 (2H, d, J=8.3 Hz), 7.10 (1H, d, J=7.8 Hz), 7.23 (2H, d, J=8.3 Hz), 7.48 (1H, t, J=7.8 Hz)

REFERENCE PRODUCTION EXAMPLE 7

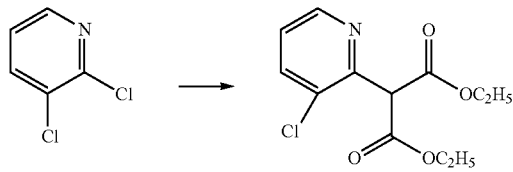 [SMILES: Clc1cccnc1Cl ; CCOC(=O)C(C(=O)OCC)c1ncccc1Cl]

8.73 g of sodium hydride (55% oil dispersion) was suspended in 100 ml of 1,4-dioxane. Into this, 32.03 g of diethyl malonate was added dropwise over a period of about 1 hour at 60° C. under a nitrogen atmosphere. The mixture was stirred at the same temperature further for 0.5 hours, then, to the mixture was added 8.26 g of copper chloride (I). Thereafter, into the mixture, a solution prepared by dissolving 12.23 g of 2,3-dichloropyridine in 50 ml of 1,4-dioxane was added dropwise at 80° C. The mixture was stirred for 22.5 hours under reflux with heating. The reaction mixture was allowed to cool to room temperature, and to the reaction mixture was added 15 ml of concentrated hydrochloric acid. To the mixture were added water and ethyl acetate, and the mixture was filtrated through celite. The filtrate was liquid-separated. The organic layer was washed with saturated brine, and dried over anhydrous magnesium sulfate, and concentrated under reduced pressure. 46.65 g of the resultant residue was subjected to silica gel column chromatography, to obtain 3.90 g of diethyl (3-chloro-2-pyridyl)malonate.

$^1$H-NMR (CDCl$_3$, TMS) δ (ppm): 1.29 (6H, t, J=7.1 Hz), 4.29 (4H, q, J=7.1 Hz), 5.22 (1H, s), 7.23 (1H, dd, J=8.1, 4.6 Hz), 7.71 (1H, dd, J=4.6, 1.5 Hz), 8.49 (1H, dd, J=4.6, 1.5 Hz)

REFERENCE PRODUCTION EXAMPLE 8

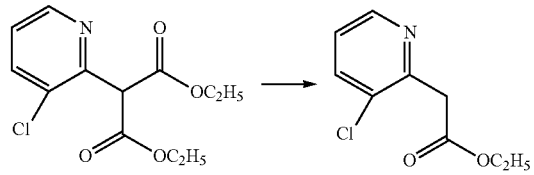 [SMILES: CCOC(=O)C(C(=O)OCC)c1ncccc1Cl ; CCOC(=O)Cc1ncccc1Cl]

3.70 g of diethyl (3-chloro-2-pyridyl)malonate and 15 ml of dimethyl sulfoxide were mixed. To the mixture was added 0.95 g of sodium chloride and 0.49 g of water. The mixture was stirred for about 20 minutes at an inner temperature of 135 to 150° C. The reaction mixture was allowed to cool to room temperature, then, water was added to the reaction mixture, and extracted with ethyl acetate. After liquid separation, the organic layer was washed with saturated brine twice, and dried over anhydrous magnesium sulfate, then, concentrated under reduced pressure to obtain 2.57 g of ethyl (3-chloro-2-pyridyl)acetate.

$^1$H-NMR (CDCl$_3$, TMS) δ (ppm): 1.27 (3H, t, J=7.1 Hz), 4.02 (2H, s), 4.21 (2H, q, J=7.1 Hz), 7.19 (1H, dd, J=8.0, 4.6 Hz), 7.69 (1H, d, J=8.0 Hz), 8.47 (1H, d, J=4.6 Hz)

REFERENCE PRODUCTION EXAMPLE 9

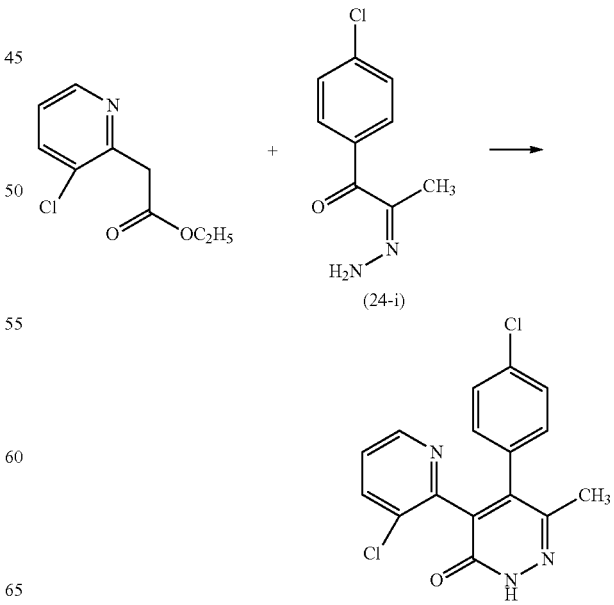

1.97 g of a compound of the formula (24-i), 2.22 g of ethyl (3-chloro-2-pyridyl)acetate, 4.08 g of sodium ethoxide (20% ethanol solution) and 35 ml of ethanol were mixed. The mixture was stirred for 2 hours under reflux with heating. The reaction mixture was allowed to cool to room temperature, then, to the reaction mixture were added ice and 6 ml of 1.71 mol/L hydrochloric acid sequentially. The resulted solid was collected by filtration. The solid was washed with water (four times), cold ethanol (twice) and cold tert-butyl methyl ether (once) sequentially, then, dried, to obtain 1.48 g of 5-(4-chlorophenyl)-4-(3-chloro-2-pyridyl)-6-methyl-2H-pyridazin-3-one.

$^1$H-NMR (CDCl$_3$, TMS) δ (ppm): 2.13 (3H, s), 7.10 (2H, br), 7.14 (1H, dd, J=8.0, 4.6 Hz), 7.23 (2H, d, J=8.8 Hz), 7.61 (1H, dd, J=8.0, 1.5 Hz), 8.41 (1H, dd, J=4.6, 1.5 Hz)

REFERENCE PRODUCTION EXAMPLE 10

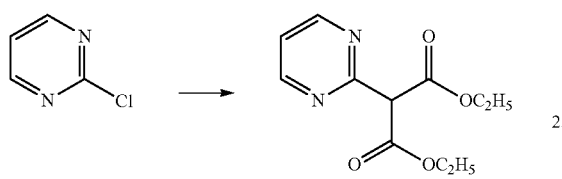

4.80 g of sodium hydride (55% oil dispersion) was suspended in 50 ml of N,N-dimethylformamide. Into this, 17.60 g of diethyl malonate was added dropwise over a period of about 0.5 hours at room temperature under a nitrogen atmosphere. The mixture was stirred further for 0.5 hours at the same temperature, then, to the mixture was added 5.73 g of 2-chloropyrimidine. The mixture was stirred for 3 hours at 100° C. The reaction mixture was allowed to cool to room temperature. To the reaction mixture was added ice water, and extracted with ethyl acetate. The organic layer was washed with saturated brine three times, dried over anhydrous magnesium sulfate, and concentrated under reduced pressure. 18.84 g of the resultant residue was subjected to silica gel column chromatography, to obtain 5.09 g of diethyl (2-pyrimidinyl)malonate.

$^1$H-NMR (CDCl$_3$, TMS) δ (ppm): 1.29 (6H, t, J=7.1 Hz), 4.29 (4H, q, J=7.1 Hz), 5.11 (1H, s), 7.26 (1H, t, J=5.1 Hz), 8.75 (1H, d, J=5.1 Hz)

REFERENCE PRODUCTION EXAMPLE 11

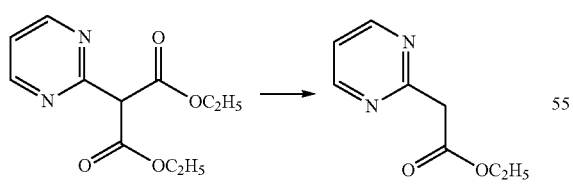

4.76 g of diethyl (2-pyrimidinyl)malonate and 20 ml of dimethyl sulfoxide were mixed. To the mixture was added 1.40 g of sodium chloride and 0.72 g of water. The mixture was stirred for about 20 minutes at an inner temperature of 140 to 145° C., and for about 20 minutes at an inner temperature of 145 to 148° C. The mixture was allowed to cool to room temperature, then, to the reaction mixture was added water, and extracted with ethyl acetate. The organic layer was washed with saturated brine twice, and dried over anhydrous magnesium sulfate, then, concentrated under reduced pressure to obtain 2.12 g of ethyl (2-pyrimidinyl)acetate.

$^1$H-NMR (CDCl$_3$, TMS) δ (ppm): 1.27 (3H, t, J=7.3 Hz), 4.04 (2H, s), 4.22 (2H, q, J=7.3 Hz), 7.21 (1H, t, J=5.1 Hz), 8.72 (2H, d, J=5.1 Hz)

REFERENCE PRODUCTION EXAMPLE 12

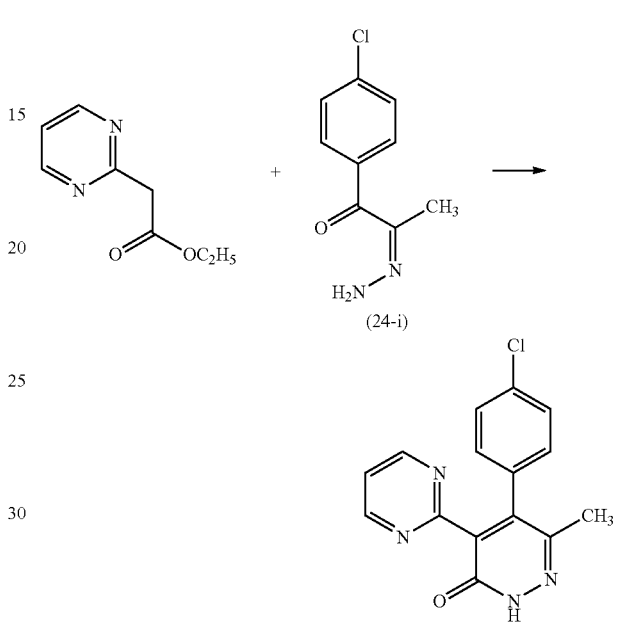

1.97 g of a compound of the formula (24-i), 1.84 g of ethyl (2-pyrimidinyl)acetate, 4.08 g of sodium ethoxide (20% ethanol solution) and 35 ml of ethanol were mixed. The mixture was stirred for 6 hours under reflux with heating. The reaction mixture was allowed to cool to room temperature, the, to the reaction mixture were added ice and 6 ml of 1.71 mol/L hydrochloric acid sequentially, and extracted with ethyl acetate. The organic layer was washed with saturated brine, dried over anhydrous magnesium sulfate, then, mostly concentrated under reduced pressure. The resultant solid was collected by filtration, and the solid was dried under reduced pressure, to obtain 1.63 g of 5-(4-chlorophenyl)-6-methyl-4-(2-pyrimidinyl)-2H-pyridazin-3-one.

$^1$H-NMR (CDCl$_3$+DMSO-d$_6$, TMS) δ (ppm): 2.13 (3H, s), 7.07 (2H, d, J=8.8 Hz), 7.13 (1H, t, J=5.1 Hz), 7.23 (2H, d, J=8.8 Hz), 8.66 (2H, d, J=5.1 Hz), 12.00 (1H, br s)

REFERENCE PRODUCTION EXAMPLE 13

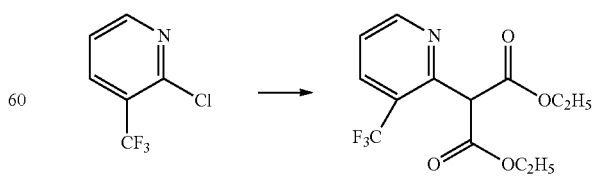

8.73 g of sodium hydride (55% oil dispersion) was suspended in 100 ml of 1,4-dioxane. Into this, 32.03 g of diethyl malonate was added dropwise over a period of about 1 hour at 60° C. under a nitrogen atmosphere. The mixture was stirred further for 0.5 hours at the same temperature, then, 8.26 g of copper chloride (I) was added to the mixture. Thereafter, into the mixture, a solution prepared by dissolving 15.00 g of 2-chloro-3-(trifluoromethyl)pyridine in 50 ml of 1,4-dioxane at 80° C. was dropped. The mixture was stirred for 16 hours under reflux with heating. The reaction mixture was allowed to cool to room temperature, and to the reaction mixture was added 15 ml of concentrated hydrochloric acid. To the mixture were added water and ethyl acetate, and the mixture was filtrated through celite. The filtrate was liquid-separated. The organic layer was washed with saturated brine, dried over anhydrous magnesium sulfate, and concentrated under reduced pressure. 51.14 g of the resultant residue was subjected to silica gel column chromatography, to obtain 6.90 g of diethyl (3-trifluoromethyl-2-pyridyl)malonate.

$^1$H-NMR (CDCl$_3$, TMS) δ (ppm): 1.27 (6H, t, J=7.1 Hz), 4.27 (4H, q, J=7.1 Hz), 5.21 (1H, s), 7.40 (1H, dd, J=8.0, 4.9 Hz), 7.99 (1H, d, J=8.0 Hz), 8.80 (1H, d, J=4.9 Hz)

REFERENCE PRODUCTION EXAMPLE 14

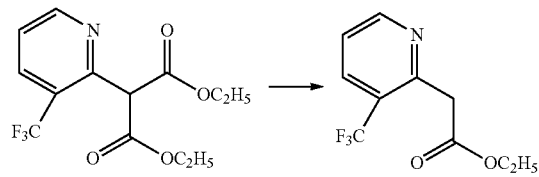 [SMILES: CCOC(=O)C(C(=O)OCC)c1ncccc1C(F)(F)F ; CCOC(=O)Cc1ncccc1C(F)(F)F]

6.10 g of diethyl (3-trifluoromethyl-2-pyridyl)malonate and 20 ml of dimethyl sulfoxide were mixed. To the mixture was added 1.40 g of sodium chloride and 0.72 g of water. The mixture was stirred for about 20 minutes at an inner temperature of 132 to 145° C. The reaction mixture was allowed to cool to room temperature, then, to the reaction mixture was added water, and extracted with ethyl acetate. The organic layer was washed with saturated brine twice, and dried over anhydrous magnesium sulfate, then, concentrated under reduced pressure, to obtain 4.64 g of ethyl (3-trifluoromethyl-2-pyridyl)acetate.

$^1$H-NMR (CDCl$_3$, TMS) δ (ppm): 1.25 (3H, t, J=7.1 Hz), 4.06 (2H, s), 4.20 (2H, q, J=7.1 Hz), 7.35 (1H, dd, J=8.0, 4.9 Hz), 7.97 (1H, d, J=8.0 Hz), 8.75 (1H, d, J=4.9 Hz)

REFERENCE PRODUCTION EXAMPLE 15

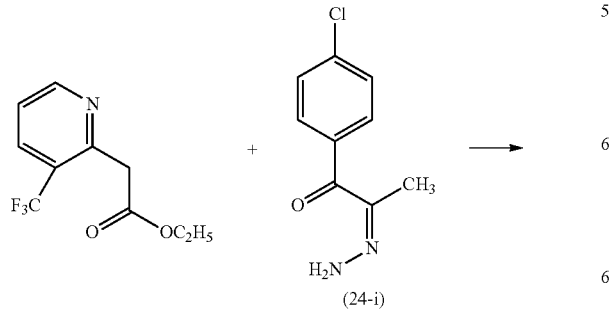

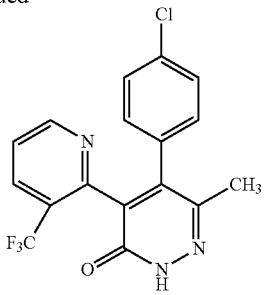

1.97 g of a compound of the formula (24-i), 2.33 g of ethyl (3-trifluoromethyl-2-pyridyl)acetate, 3.40 g of sodium ethoxide (20% ethanol solution) and 35 ml of ethanol were mixed. The mixture was stirred for 5 hours under reflux with heating. The reaction mixture was allowed to cool to room temperature, then, to the reaction mixture were added ice and 8.3 ml of 1.2 mol/L hydrochloric acid sequentially, and extracted with ethyl acetate. The organic layer was washed with saturated brine, and dried over anhydrous magnesium sulfate, then, concentrated under reduced pressure. 2.93 g of the resultant residue was subjected to silica gel column chromatography, to obtain 0.92 g of 5-(4-chlorophenyl)-6-methyl-4-(3-trifluoromethyl-2-pyridyl)-2H-pyridazin-3-one.

$^1$H-NMR (CDCl$_3$+DMSO-d$_6$ one drop, TMS) δ (ppm): 2.13 (3H, s), 7.06 (2H, br), 7.20 (2H, br d), 7.30-7.35 (1H), 7.87 (1H, d), 8.75 (1H, d)

REFERENCE PRODUCTION EXAMPLE 16

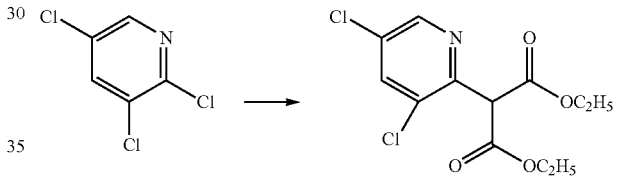

A mixture of 4.56 g 2,3,5-trichloropyridine, 8.80 g of diethyl malonate, 30 ml of dimethyl sulfoxide and 17.9 g of cesium carbonate was stirred for 8 hours at 110° C. under a nitrogen atmosphere. The reaction mixture was allowed to cool to room temperature, then, to this was added ice water, and extracted with ethyl acetate. The organic layer was washed with saturated brine twice, and dried over anhydrous magnesium sulfate, then, concentrated under reduced pressure. 7.45 g of the resultant residue was subjected to silica gel column chromatography, to obtain 7.08 g of diethyl (3,5-dichloro-2-pyridyl)malonate.

$^1$H-NMR (CDCl$_3$, TMS) δ (ppm): 1.28 (6H, t, J=7.1 Hz), 4.28 (4H, q, J=7.1 Hz), 5.16 (1H, s), 7.74 (1H, d, J=2.2 Hz), 8.45 (1H, d, J=2.2 Hz)

REFERENCE PRODUCTION EXAMPLE 17

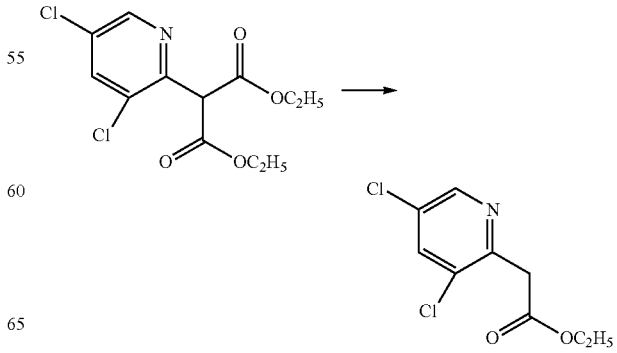

6.75 g of diethyl (3,5-dichloro-2-pyridyl)malonate and 20 ml of dimethyl sulfoxide were mixed. To the mixture was added 1.57 g of sodium chloride and 0.79 g of water. The mixture was stirred for about 40 minutes at an inner temperature of 135 to 150° C. The mixture was allowed to cool to room temperature, then, water was added to the reaction mixture, and extracted with ethyl acetate. The organic layer was washed with saturated brine twice, and dried over anhydrous magnesium sulfate, then, concentrated under reduced pressure, to obtain 4.76 g of ethyl (3,5-dichloro-2-pyridyl)acetate.

$^1$H-NMR (CDCl$_3$, TMS) δ (ppm): 1.25 (3H, t, J=7.1 Hz), 3.98 (2H, s), 4.18 (2H, q, J=7.1 Hz), 7.72 (1H, d, J=2.2 Hz), 8.42 (1H, d, J=2.2 Hz)

REFERENCE PRODUCTION EXAMPLE 18

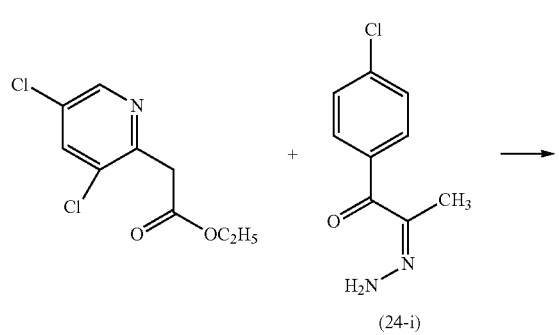

(24-i)

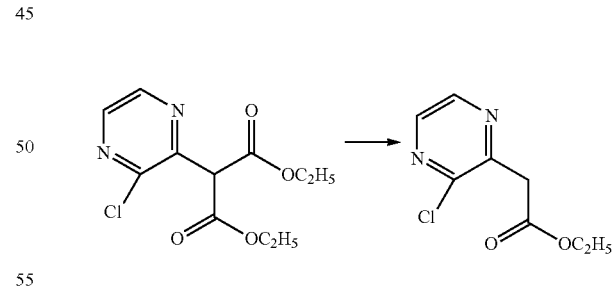

3.74 g of a compound of the formula (24-i), 4.47 g of ethyl (3,5-dichloro-2-pyridyl)acetate, 6.46 g of sodium ethoxide (20% ethanol solution) and 50 ml of ethanol were mixed. The mixture was stirred for 2 hours under reflux with heating. The reaction mixture was allowed to cool to room temperature, then, to the reaction mixture were added ice and 10 ml of 1.71 mol/L hydrochloric acid sequentially. The generated solid was collected by filtration. The solid was washed with water (four times), cold ethanol (twice) and cold tert-butyl methyl ether (once) sequentially, then, dried to obtain 3.51 g of solid. To this solid was added 50 ml of butanol, and the mixture was stirred for 20 minutes on an oil bath of 120° C., then, cooled. The generated solid was collected by filtration, and washed with a mixed solvent of tert-butyl methyl ether and hexane, to obtain 2.71 g of 5-(4-chlorophenyl)-4-(3,5-dichloro-2-pyridyl)-6-methyl-2H-pyridazin-3-one.

$^1$H-NMR (CDCl$_3$+DMSO-d$_6$ one drop, TMS) δ (ppm): 2.12 (3H, s), 7.08 (2H, br), 7.26 (2H, d, J=8.8 Hz), 7.64 (1H, d, J=2.0 Hz), 8.37 (1H, d, J=2.0 Hz), 12.18 (1H, br s),

REFERENCE PRODUCTION EXAMPLE 19

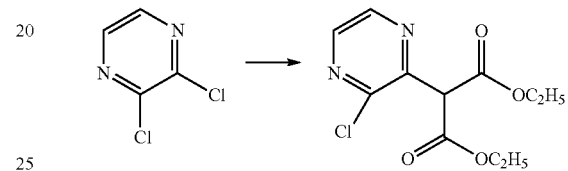

A mixture of 3.73 g of 2,3-dichloropyrazine, 8.80 g of diethyl malonate, 30 ml of dimethyl sulfoxide and 17.9 g of cesium carbonate was stirred for 8 hours at 110° C. under a nitrogen atmosphere. The reaction mixture was allowed to cool to room temperature, then, to this was added ice water and extracted with ethyl acetate. The organic layer was washed with saturated brine twice, and dried over anhydrous magnesium sulfate, then, concentrated under reduced pressure. 3.67 g of the resultant residue was subjected to silica gel column chromatography, to obtain 2.69 g of diethyl (3-chloro-2-pyrazinyl)malonate.

$^1$H-NMR (CDCl$_3$, TMS) δ (ppm): 1.27 (6H, t, J=7.2 Hz), 4.30 (4H, q, J=7.2 Hz), 5.20 (1H, s), 8.36 (1H, d, J=2.6 Hz), 8.50 (1H, d, J=2.6 Hz)

REFERENCE PRODUCTION EXAMPLE 20

2.42 g of diethyl (3-chloro-2-pyrazinyl)malonate and 15 ml of dimethyl sulfoxide were mixed. To the mixture was added 0.62 g of sodium chloride and 0.32 g of water. The mixture was stirred for about 35 minutes at an inner temperature of 127 to 153° C. The reaction mixture was allowed to cool to room temperature, then, to the reaction mixture was added water, and extracted with ethyl acetate. The organic layer was washed with saturated brine twice, and dried over anhydrous magnesium sulfate, then, concentrated under reduced pressure, to obtain 1.53 g of ethyl (3-chloro-2-pyrazinyl)acetate.

$^1$H-NMR (CDCl$_3$, TMS) δ (ppm): 1.27 (3H, t, J=7.1 Hz), 4.09 (2H, s), 4.22 (2H, q, J=7.1 Hz), 8.31 (1H, d, J=2.4 Hz), 8.47 (1H, d, J=2.4 Hz)

REFERENCE PRODUCTION EXAMPLE 21

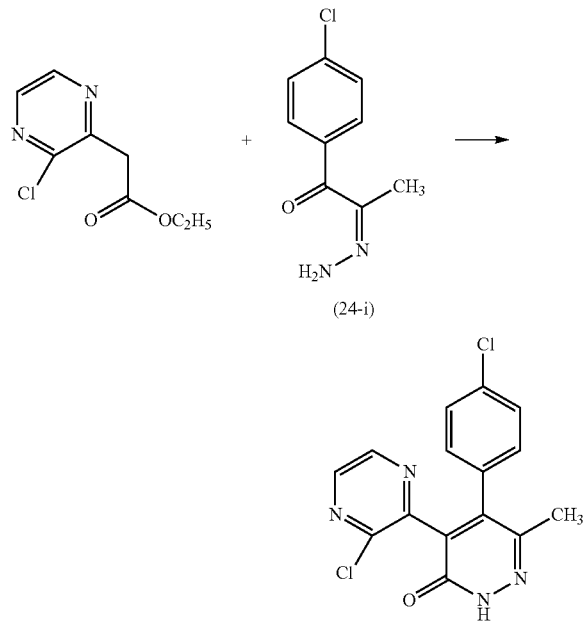

1.32 g of a compound of the formula (24-i), 1.35 g of ethyl (3-chloro-2-pyrazyl)acetate, 2.29 g of sodium ethoxide (20% ethanol solution) and 20 ml ethanol were mixed. The mixture was stirred for 2 hours under reflux with heating. The reaction mixture was allowed to cool to room temperature, then, to the reaction mixture were added ice and 3.5 ml of 1.71 mol/L hydrochloric acid sequentially. The generated solid was collected by filtration. The solid was washed with water (four times), cold ethanol (twice) and cold tert-butyl methyl ether (once) sequentially, then, dried to obtain 1.18 g of 5-(4-chlorophenyl)-4-(3-chloro-2-pyrazyl)-6-methyl-2H-pyridazin-3-one.

$^1$H-NMR (CDCl$_3$, TMS) δ (ppm): 2.15 (3H, s), 7.08 (2H, br d, J=8.2 Hz), 7.26 (2H, d, J=8.2 Hz), 8.26 (1H, d, J=2.4 Hz), 8.42 (1H, d, J=2.4 Hz)

REFERENCE PRODUCTION EXAMPLE 22

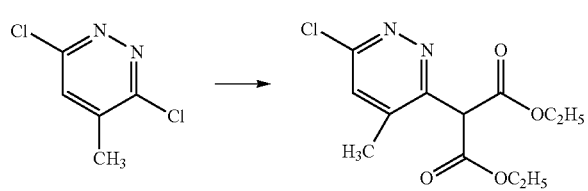

A mixture of 4.29 g of 3,6-dichloro-4-methylpyridazine, 8.80 g of diethyl malonate, 25 ml of dimethyl sulfoxide and 17.9 g of cesium carbonate was stirred for 4 hours at 110° C. under a nitrogen atmosphere. The reaction mixture was allowed to cool to room temperature, then, to this was added ice water and extracted with ethyl acetate. The organic layer was washed with saturated brine twice, and dried over anhydrous magnesium sulfate, then, concentrated under reduced pressure. 7.08 g of the resultant residue was subjected to silica gel column chromatography, to obtain 1.95 g of diethyl (6-chloro-4-methyl-3-pyridazinyl)malonate.

$^1$H-NMR (CDCl$_3$, TMS) δ (ppm): 1.30 (6H, t, J=7.2 Hz), 2.32 (3H, s), 4.28 (4H, q, J=7.2 Hz), 5.17 (1H, s), 7.36 (1H, s)

REFERENCE PRODUCTION EXAMPLE 23

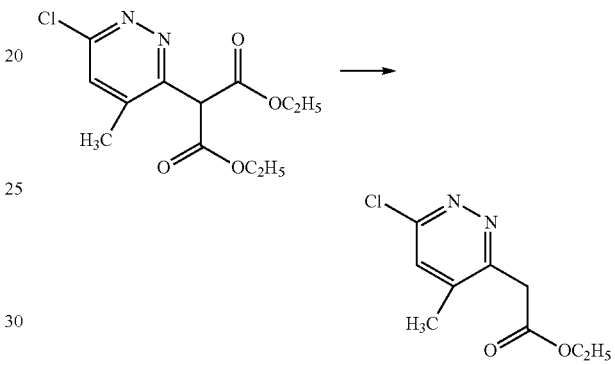

1.81 g of diethyl (6-chloro-4-methyl-3-pyridazinyl)malonate and 15 ml of dimethyl sulfoxide were mixed. To the mixture was added 0.45 g of sodium chloride and 0.23 g of water. The mixture was stirred for about 40 minutes at an inner temperature of 125 to 150° C. The reaction mixture was allowed to cool to room temperature, then, to the reaction mixture was added water, and extracted with ethyl acetate. The organic layer was washed with saturated brine twice, and dried over anhydrous magnesium sulfate, then, concentrated under reduced pressure. 1.05 g of the resultant residue was subjected to silica gel column chromatography, to obtain 0.91 g of ethyl (6-chloro-4-methyl-3-pyridazinyl)acetate.

$^1$H-NMR (CDCl$_3$, TMS) δ (ppm): 1.27 (3H, t, J=7.2 Hz), 2.34 (3H, s), 4.07 (2H, s), 4.20 (2H, q, J=7.2 Hz), 7.33 (1H, s)

REFERENCE PRODUCTION EXAMPLE 24

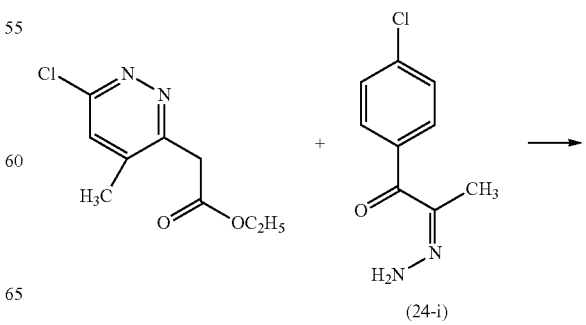

-continued

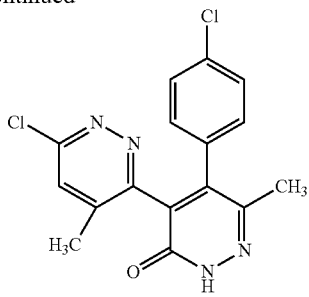

0.69 g of a compound of the formula (24-i), 0.75 g of ethyl (6-chloro-4-methyl-3-pyridazinyl)acetate, 1.19 g of sodium ethoxide (20% ethanol solution) and 10 ml of ethanol were mixed. The mixture was stirred for 2 hours under reflux with heating. The reaction mixture was allowed to cool to room temperature, then, ice and 2.4 ml of 1.2 mol/L hydrochloric acid and water were added sequentially. To the reaction mixture was added water, and extracted with ethyl acetate. The organic layer was washed with saturated brine, and dried over anhydrous magnesium sulfate, then, concentrated under reduced pressure. 1.06 g of the resultant residue was subjected to silica gel column chromatography, to obtain 0.37 g of 5-(4-chlorophenyl)-4-(6-chloro-4-methyl-3-pyridazinyl)-6-methyl-2H-pyridazin-3-one.

$^1$H-NMR (CDCl$_3$, TMS) δ (ppm): 2.15 (3H, s), 2.22 (3H, s), 6.75-6.9 (2H, br), 7.28 (1H, s), 7.2-7.4 (2H, br), 11.63 (1H, br s)

REFERENCE PRODUCTION EXAMPLE 25

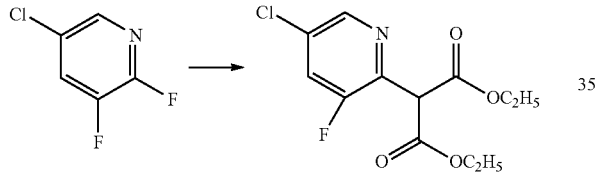

A mixture of 3.85 g of 5-chloro-2,3-difluoropyridine, 8.80 g of diethyl malonate, 25 ml of dimethyl sulfoxide and 17.9 g of cesium carbonate was stirred for 4.5 hours at 110° C. under a nitrogen atmosphere. The reaction mixture was allowed to cool to room temperature, then, to this was added ice water, and extracted with ethyl acetate. The organic layer was washed with saturated brine twice, and dried over anhydrous magnesium sulfate, then, concentrated under reduced pressure, to obtain 5.83 g of diethyl (5-chloro-3-fluoro-2-pyridyl)malonate.

$^1$H-NMR (CDCl$_3$, TMS) δ (ppm): 1.29 (6H, t, J=7.1 Hz), 4.28 (4H, q, J=7.1 Hz), 5.03 (1H, s), 7.49 (1H, dd, J=9.0, 2.0 Hz), 8.39 (1H, d, J=2.0 Hz)

REFERENCE PRODUCTION EXAMPLE 26

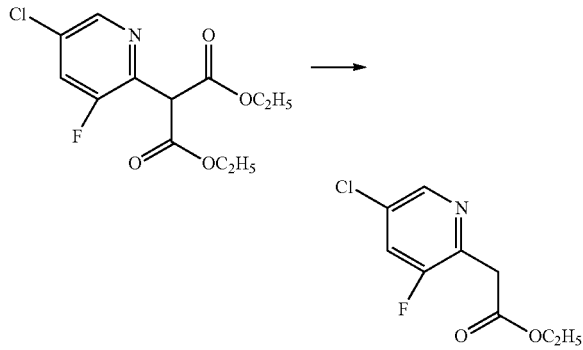

5.83 g of diethyl (5-chloro-3-fluoro-2-pyridyl)malonate and 25 ml of dimethyl sulfoxide were mixed. To the mixture were added 1.29 g of sodium chloride and 0.72 g of water. The mixture was stirred for about 40 minutes at an inner temperature of 135 to 142° C. The reaction mixture was allowed to cool to room temperature, then, to the reaction mixture was added water, and extracted with ethyl acetate. The organic layer was washed with saturated brine twice, and dried over anhydrous magnesium sulfate, then, concentrated under reduced pressure. 4.03 g of the resultant residue was subjected to silica gel column chromatography, to obtain 3.16 g of ethyl (5-chloro-3-fluoro-2-pyridyl)acetate.

$^1$H-NMR (CDCl$_3$, TMS) δ (ppm): 1.26 (3H, t, J=7.1 Hz), 3.92 (2H, s), 4.21 (2H, q, J=7.1 Hz), 7.46 (1H, dd, J=8.8, 2.0 Hz), 8.36 (1H, d, J=2.0 Hz)

REFERENCE PRODUCTION EXAMPLE 27

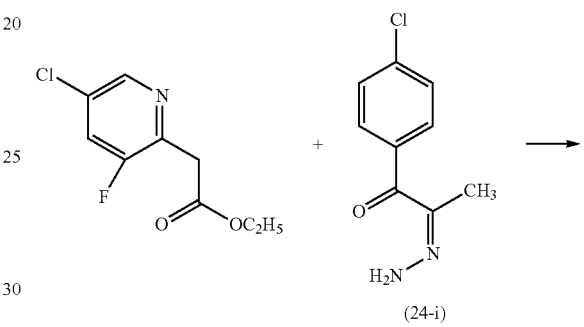

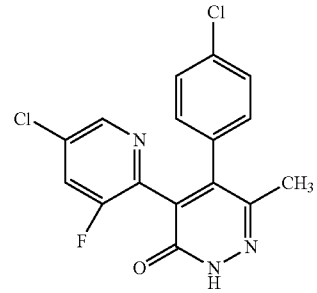

0.88 g of a compound of the formula (24-i), 1.24 g of ethyl (5-chloro-3-fluoro-2-pyridyl)acetate, 1.71 g of sodium ethoxide (20% ethanol solution) and 15 ml ethanol were mixed. The mixture was stirred for 2 hours under reflux with heating. The reaction mixture was allowed to cool to room temperature, then, to the reaction mixture were added ice and 1.7 mol/L hydrochloric acid and water sequentially, and extracted with ethyl acetate. The organic layer was washed with saturated brine, and dried over anhydrous magnesium sulfate, then, concentrated under reduced pressure. 1.43 g of the resultant residue was subjected to silica gel column chromatography, to obtain 0.40 g of 5-(4-chlorophenyl)-4-(5-chloro-3-fluoro-2-pyridyl)-6-methyl-2H-pyridazin-3-one.

$^1$H-NMR (CDCl$_3$, TMS) δ (ppm): 2.13 (3H, s), 6.95-7.15 (2H, br), 7.28 (2H, d, J=8.8 Hz), 7.35 (1H, dd, J=8.6, 2.0 Hz), 8.33 (1H

REFERENCE PRODUCTION EXAMPLE 28

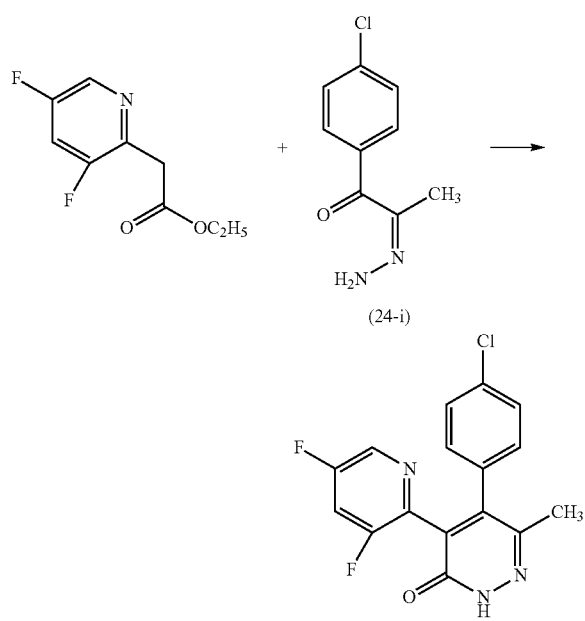

0.36 g of a compound of the formula (24-i), 0.37 g of ethyl (3,5-difluoro-2-pyridyl)acetate, 0.63 g of sodium ethoxide (20% ethanol solution) and 10 ml of ethanol were mixed. The mixture was stirred for 2 hours under reflux with heating. The reaction mixture was allowed to cool to room temperature, then, to the reaction mixture were added ice and 1.0 ml of 1.2 mol/L hydrochloric acid sequentially, and extracted with ethyl acetate. The organic layer was washed with saturated brine, and dried over anhydrous magnesium sulfate, then, concentrated under reduced pressure. 0.54 g of the resultant residue was subjected to silica gel column chromatography (hexane-ethyl acetate gradient), to obtain 0.14 g of 5-(4-chlorophenyl)-4-(3,5-difluoro-2-pyridyl)-6-methyl-2H-pyridazin-3-one.

$^1$H-NMR (CDCl$_3$, TMS) δ (ppm): 2.13 (3H, s), 6.95-7.15 (2H, br), 7.10 (2H, d, J=7.8 Hz), 8.26 (1H, d, J=2.4 Hz), 10.94 (1H, br)

REFERENCE PRODUCTION EXAMPLE 29

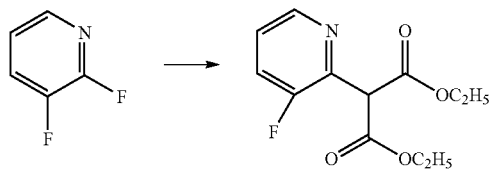

A mixture of 3.95 g of 2,3-difluoropyridine, 13.2 g of diethyl malonate, 38 ml of dimethyl sulfoxide and 26.85 g of cesium carbonate was stirred for 3 hours at 100° C. under a nitrogen atmosphere. The reaction mixture was allowed to cool to room temperature, then, to this was added ice water and extracted with ethyl acetate. The organic layer was washed with saturated brine twice, and dried over anhydrous magnesium sulfate, then, concentrated under reduced pressure. 12.18 g of the resultant residue was subjected to silica gel column chromatography, to obtain 6.38 g of diethyl (3-fluoro-2-pyridyl)malonate.

$^1$H-NMR (CDCl$_3$, TMS) δ (ppm): 1.28 (6H, t, J=7.2 Hz), 4.28 (4H, q, J=7.2 Hz), 5.08 (1H, s), 7.30 (1H, m), 7.43 (1H, m), 8.41 (1H)

REFERENCE PRODUCTION EXAMPLE 30

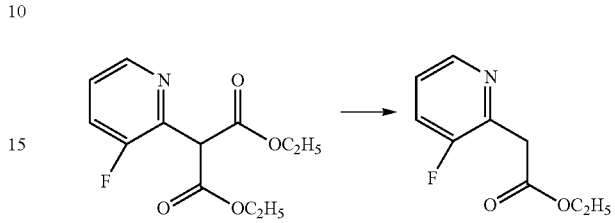

5.10 g of diethyl (3-fluoro-2-pyridyl)malonate and 25 ml of dimethyl sulfoxide were mixed. To the mixture was added 1.29 g of sodium chloride and 0.72 g of water. The mixture was stirred for about 40 minutes at an inner temperature of 145 to 152° C. The reaction mixture was allowed to cool to room temperature, then, to the reaction mixture was added water, and extracted with ethyl acetate. The organic layer was washed with saturated brine twice, and dried over anhydrous magnesium sulfate, then, concentrated under reduced pressure, to obtain 2.99 g of ethyl (3-fluoro-2-pyridyl)acetate.

$^1$H-NMR (CDCl$_3$, TMS) δ (ppm): 1.26 (3H, t, J=7.2 Hz), 3.92 (2H, s), 4.19 (2H, q, J=7.2 Hz), 7.23 (1H, m), 7.39 (1H, m), 8.38 (1H, m)

REFERENCE PRODUCTION EXAMPLE 31

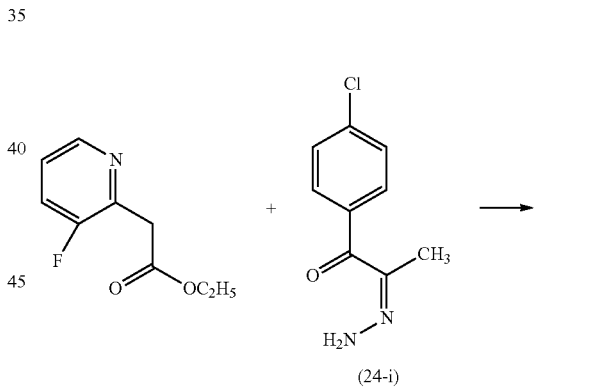

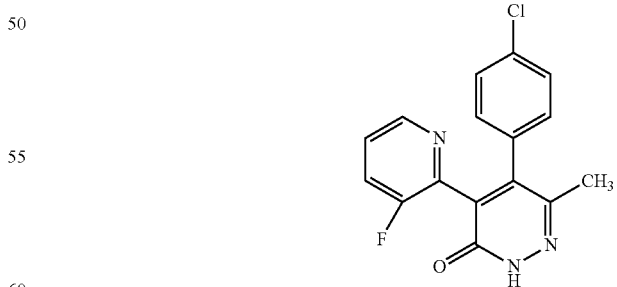

1.97 g of a compound of the formula (24-i), 1.83 g of ethyl (3-fluoro-2-pyridyl)acetate, 4.08 g of sodium ethoxide (20% ethanol solution) and 25 ml of ethanol were mixed. The mixture was stirred for 2 hours under reflux with heating. The reaction mixture was allowed to cool to room temperature, then, to the reaction mixture were added ice and 8 ml of 1.2 mol/L hydrochloric acid sequentially, and extracted with ethyl acetate. The organic layer was washed with saturated brine, and dried over anhydrous magnesium sulfate, then, concentrated under reduced pressure. 2.62 g of the resultant residue was subjected to silica gel column chromatography, to obtain 1.32 g of 5-(4-chlorophenyl)-4-(3-fluoro-2-pyridyl)-6-methyl-2H-pyridazin-3-one.

$^1$H-NMR (CDCl$_3$, TMS) δ (ppm): 2.13 (3H, s), 6.95-7.15 (2H, br), 7.15-7.35 (4H), 8.34 (1H, m), 10.91 (1H, br s)

Next, formulation examples are shown. Here, parts are by weight.

FORMULATION EXAMPLE 1

Each 50 parts of the compounds (1) to (16) of the present invention, 3 parts of calcium ligninsulfonate, 2 parts of magnesium laurylsulfate and 45 parts of synthetic hydrated silica are pulverlized and mixed thoroughly to obtain wettable powders.

FORMULATION EXAMPLE 2

Each 20 parts of the compounds (1) to (16) of the present invention and 1.5 parts of sorbitan trioleate are mixed with 28.5 parts of an aqueous solution containing 2 parts of polyvinyl alcohol and wet-pulverized finely, then, into this was added 40 parts of an aqueous solution containing 0.05 parts of xanthan gum and 0.1 part of aluminum magnesium silicate, and further, 10 parts of propylene glycol was added and mixed while stirring to obtain flowable formulations.

FORMULATION EXAMPLE 3

Each 2 parts of the compounds (1) to (16) of the present invention, 88 parts of kaolin clay and 10 parts of talc are pulverized and mixed thoroughly to obtain dusts.

FORMULATION EXAMPLE 4

Each 5 parts of the compounds (1) to (16) of the present invention, 14 parts of polyoxyethylene styryl phenyl ether, 6 parts of calcium dodecylbenzenesulfonate and 75 parts of xylene were mixed thoroughly to obtain emulsifiable concentrates.

FORMULATION EXAMPLE 5

Each 2 parts of the compounds (1) to (16) of the present invention, 1 part of synthetic hydrated silica, 2 parts of calcium ligninsulfonate, 30 parts of bentonite and 65 parts of kaolin clay are pulverized and mixed thoroughly, then, water was added and kneaded thoroughly, and granulated and dried, to obtain granules.

FORMULATION EXAMPLE 6

Each 10 parts of the compounds (1) to (16) of the present invention, 35 parts of white carbon containing 50 wt % of polyoxyethylene alkyl ether sulfate ammonium salt and 55 parts of water are mixed, and wet pulverized finely, to obtain formulations.

Next, effectiveness of the compound of the present invention on control of plant diseases will be shown by test examples.

TEST EXAMPLE 1

A plastic pot was filled with sandy loam, Japanese radish (cultivar: WASE 40 days) was sowed and grown in a greenhouse for 5 days. The formulations of the compounds (1) to (3), (5), (6), (9) to (12) and (14) to (16) of the present invention obtained according to Formulation Example 6 were diluted with water to give a concentration of 500 ppm. The resultant diluted liquids were sprayed on stem and leaves so that they sufficiently adhered to the surface of the leaf of the above-described radish. After spraying, the plant was air-dried, and spores of *Alternaria brassicicola* were inoculated. Then, the radish was left overnight at 23° C. under humid condition, further, allowed to stand for 3 days in a greenhouse, then, the controlling effect was checked. As a result, the lesion areas on radish treated with the compounds (1) to (3), (5), (6), (9) to (12) and (14) to (16) of the present invention were 30% or less with respect to the lesion area on non-treated districts.

TEST EXAMPLE 2

A plastic pot was filled with sandy loam, cucumber (cultivar: SAGAMI HANJIRO) was sowed and grown in a greenhouse for 10 days. The formulations of the compounds (1) to (3) and (5) to (16) of the present invention obtained according to Formulation Example 6 were diluted with water to give a concentration of 500 ppm. The resultant diluted liquids were sprayed on stem and leaves so that they sufficiently adhered to the surface of the leaf of the above-described cucumber. After spraying, the plant was air-dried, and a PDA medium containing spores of *Botrytis cinerea* was placed on the surface of seminal leaf of cucumber. Then, the cucumber was left for 5 days at 12° C. under humid condition, then, the lesion area of the plant was visually observed. As a result, the lesion areas on cucumber treated with the compounds (1) to (3) and (5) to (16) of the present invention were 50% or less with respect to the lesion area on non-treated districts.

TEST EXAMPLE 3

A plastic pot was filled with sandy loam, paddy (cultivar: NIHONBARE) was sowed and grown in a greenhouse for 20 days. The formulations of the compounds (1) to (3) and (5) to (16) of the present invention obtained according to Formulation Example 6 were diluted with water to give a concentration of 200 ppm. The resultant diluted liquids were sprayed on stem and leaves so that they sufficiently adhered to the surface of the leaf of the above-described paddy. After spraying, the plant was air-dried. Bran-cultured mycelia of *Rhizoctonia solani* was placed around the bottom of paddy stock, and left for 6 days at 28° C. under humid condition. Thereafter, the controlling effect was checked. As a result, the lesion areas on paddy treated with the compounds (1) to (3) and (5) to (16) of the present invention were 50% or less with respect to the lesion area on non-treated districts.

TEST EXAMPLE 4

A plastic pot was filled with sandy loam, cucumber (cultivar: SAGAMI HANJIRO) was sowed and grown in a greenhouse for 12 days. The formulations of the compounds (1) to (3), (5) to (7), (9) to (12) and (14) to (16) of the present invention obtained according to Formulation Example 6 were diluted with water to give a concentration of 200 ppm. The resultant diluted liquids were sprayed on stem and leaves so that they sufficiently adhered to the surface of the leaf of the above-described cucumber. After spraying, the plant was air-dried, and spores of *Sphaerotheca fuliginea* were inoculated. Then, the cucumber was left for 12 days at 23° C., then, the controlling effect was checked. As a result, the lesion areas on cucumber treated with the compounds (1) to (3), (5) to (7), (9) to (12) and (14) to (16) of the present invention were 10% or less with respect to the lesion area on non-treated districts.

INDUSTRIAL APPLICABILITY

By use of the compound of the present invention, plant diseases can be controlled.

The invention claimed is:

1. A compound of the formula (2):

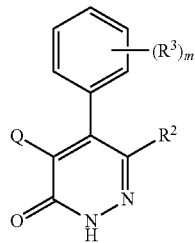

(2)

(wherein, $R^2$ represents a C1-C4 alkyl group, $R^3$ represents a halogen atom, nitro group, cyano group, C1-C4 alkyl group optionally substituted with at least one halogen atom, C1-C4 alkoxy group optionally substituted with at least one halogen atom or C1-C4 alkylthio group optionally substituted with at least one halogen atom, m represents an integer of 0 to 5, and when m is an integer of 2 or more, $R^3$ s are mutually the same or different, Q represents a 6-membered aromatic heterocyclic group having at least one nitrogen atom as a ring constituent atom, and the aromatic heterocyclic group is optionally substituted with at least one substituent selected from the group consisting of halogen atoms, nitro group, cyano group, C1-C4 alkyl groups optionally substituted with at least one halogen atom and C1-C4 alkoxy groups optionally substituted with at least one halogen atom).

* * * * *